United States Patent
Jessen et al.

(10) Patent No.: US 8,178,544 B2
(45) Date of Patent: May 15, 2012

(54) 2, 3-DIAMINO-QUINAZOLINONE DERIVATIVES AND THEIR MEDICAL USE

(75) Inventors: Carsten Jessen, Birkerod (DK); William Dalby Brown, Soborg (DK); Joachim Demnitz, Copenhagen (DK); Dorte Strøbæk, Farum (DK); Mads P. G. Korsgaard, Frederiksberg (DK); Palle Christophersen, Ballerup (DK)

(73) Assignee: Neurosearch A/S, Ballerup (DK)

( * ) Notice: Subject to any disclaimer, the term of this patent is extended or adjusted under 35 U.S.C. 154(b) by 153 days.

(21) Appl. No.: 12/601,124

(22) PCT Filed: May 22, 2008

(86) PCT No.: PCT/EP2008/056322
§ 371 (c)(1),
(2), (4) Date: Feb. 1, 2010

(87) PCT Pub. No.: WO2008/142140
PCT Pub. Date: Nov. 27, 2008

(65) Prior Publication Data
US 2010/0160315 A1    Jun. 24, 2010

Related U.S. Application Data

(60) Provisional application No. 60/939,723, filed on May 23, 2007.

(30) Foreign Application Priority Data

May 23, 2007 (DK) ................................. 2007 00756

(51) Int. Cl.
*A61K 31/517* (2006.01)
(52) U.S. Cl. .................. 514/266.3; 514/266.4; 544/287; 544/292
(58) Field of Classification Search .................. 544/287, 544/292
See application file for complete search history.

(56) References Cited

FOREIGN PATENT DOCUMENTS

| WO | WO-2004/058704 A2 | 7/2004 |
| WO | WO-2005/025293 A2 | 3/2005 |
| WO | WO-2007/057447 A1 | 5/2007 |
| WO | WO-2007/104717 A1 | 9/2007 |

OTHER PUBLICATIONS

Wang et al., "Positional cloning of a novel potassium channel gene: KVLQT1 mutations cause cardiac arrhythmias", Nature Genetics, vol. 12, pp. 17-23, Jan. 12, 1996.
Biervert et al., "A Potassium Channel Mutation in Neonatal Human Epilepsy", Science, vol. 279, pp. 403-406, Jan. 16, 1998.
Schroeder et al., Moderate loss of function of cyclic-AMP-modulated KCNQ2/KCNQ3 K⁺ channels causes epilepsy, Nature, vol. 396, pp. 687-690, Dec. 17, 1998.
Schroeder et al., KCNQ5, a Novel Potassium Channel Broadly Expressed in Brain, Mediates M-type Currents, The Journal of Biological Chemistry, vol. 275, No. 31, pp. 24089-24095, Aug. 4, 2000.
Kubisch et al., "KCNQ4, a Novel Potassium Channel Expressed in Sensory Outer Hair Cells, is Mutated in Dominant Deafness", Cell, vol. 96, pp. 437-446, Feb. 5, 1999.

*Primary Examiner* — James O Wilson
*Assistant Examiner* — Brian McDowell
(74) *Attorney, Agent, or Firm* — Birch, Stewart, Kolasch & Birch, LLP

(57) ABSTRACT

This invention provides 2,3-diamino-quinazolinone compounds of Formula (I)

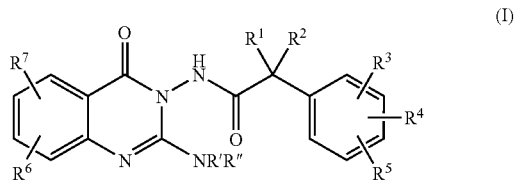

stereoisomers thereof, pharmaceutically-acceptable addition salts thereof, and N-oxides thereof, wherein the variables are as defined in the specification. The 2,3-diamino-quinazolinone compounds have medical utility. The 2,3-diamino-quinazolinone compounds can be used for the manufacture of medicaments, including pharmaceutical compositions. This invention also provides methods of treating disorders, diseases, or conditions which are responsive to activation of $K_v7$ channels.

10 Claims, No Drawings

2,3-DIAMINO-QUINAZOLINONE DERIVATIVES AND THEIR MEDICAL USE

This application is the National Phase of PCT/EP/2008/056322 filed on May 22, 2008, which claims priority under 35 U.S.C. 119(e) to U.S. Provisional Application No. 60/939,723 filed on May 23, 2007, and under 35 U.S.C. 119(a) to Patent Application No. PA 2007 00756 filed in Denmark on May 23, 2007, all of which are hereby expressly incorporated by reference into the present application.

TECHNICAL FIELD

This invention relates to novel 2,3-diamino-quinazolinone derivatives having medical utility, to use of the 2,3-diamino-quinazolinone derivatives of the invention for the manufacture of a medicament, to pharmaceutical compositions comprising the 2,3-diamino-quinazolinone derivatives of the invention, and to methods of treating a disorder, disease or a condition of a subject, which disorder, disease or condition is responsive to activation of $K_v7$ channels.

BACKGROUND ART

Potassium ($K^+$) channels are structurally and functionally diverse families of $K^+$-selective channel proteins, which are ubiquitous in cells, indicating their central importance in regulating a number of key cell functions. While widely distributed as a class, $K^+$ channels are differentially distributed as individual members of this class or as families.

Recently a new family of potassium channels, the KCNQ channels, has attracted attention as target for therapeutic development. The human KCNQ1 channel was disclosed by Wang, Q et al. [Wang, Q et al.; *Nature Genet.* 1996 12 17-23], the human KCNQ2 channel was disclosed by Biervert et al. [Biervert et al.; *Science* 1998 279 403-406]; the human KCNQ3 channel was disclosed by Schroeder et al. [Schroeder et al.; *Nature* 1998 396 687-690]; the human KCNQ4 channel was disclosed by Kubisch et al. [Kubisch et al.; *Cell* 1999 96 (3) 437-46]; and the human KCNQ5 channel was disclosed by Schroeder et al. [Schroeder et al.; *J. Biol. Chem.* 2000 275 (31) 24089-24095]. According to the latest nomenclature KCNQ1-KCNQ5 channels now are also designated $K_v7.1$-$K_v7.5$.

Due to the distribution of KCNQ channels within the organism, KCNQ channel modulators are considered potentially useful for the treatment or alleviation of conditions as diverse as pain, migraine, tension type headache, CNS disorders, CNS damage caused by trauma, stroke or neurodegenerative illness or diseases, learning and cognitive disorders, motion and motor disorders, multiple sclerosis, heart failure, cardiomyopathia, cardiac disorders, inflammatory diseases, ophthalmic conditions, progressive hearing loss or tinnitus, obstructive or inflammatory airway diseases, for inducing or maintaining bladder control including the treatment or prevention of urinary incontinence.

WO 2005/025293 discloses fused ring heterocycles useful as potassium channel modulators. However, the 2,3-diamino-quinazolinone derivatives of the present invention are not described.

SUMMARY OF THE INVENTION

It is an object of the present invention to provide novel 2,3-diamino-quinazolinone derivatives having medical utility for combating disorders, diseases or conditions responsive to activation of $K_v7$ channels.

In its first aspect the invention provides 2,3-diamino-quinazolinone derivatives of Formula (I)

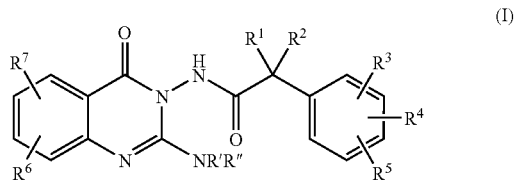

a stereoisomer or a mixture of its stereoisomers, or a pharmaceutically-acceptable addition salt thereof, or an N-oxide thereof, wherein $R^1$ represents hydrogen, alkyl or halo; and $R^2$ represents hydrogen, alkyl, cycloalkyl, halo, haloalkyl, hydroxyalkyl, hydroxy, alkoxy, phenyl, phenyl-alkyl, amino, alkyl-carbonyl-amino, cyano or nitro; or $R^1$ and $R^2$ together with the carbon atom to which they are attached form a cycloalkyl (spiro) group; or $R^1$ represents hydrogen; and $R^2$ together with one of $R^3$, $R^4$ and $R^5$, attached in ortho-position on the aromatic ring, form a —$(CH_2)_n$— bridge, wherein n is 1, 2 or 3;

$R^3$, $R^4$ and $R^5$, independently of each other, represent hydrogen, alkyl, cycloalkyl, halo, haloalkyl, hydroxy, alkoxy, haloalkoxy, amino, alkyl-carbonyl-amino, alkyl-sulfanyl, alkyl-sulfonyl, phenyl, phenoxy, benzoyl, cyano or nitro; or two of $R^3$, $R^4$ and $R^5$, together form a methylenedioxy group; and the remaining of $R^3$, $R^4$ and $R^5$ is as defined above; or two of $R^3$, $R^4$ and $R^5$, together with the phenyl ring to which they are attached, form a naphthyl group; and the remaining of $R^3$, $R^4$ and $R^5$ is as defined above, or one of $R^3$, $R^4$ and $R^5$, attached in ortho-position on the aromatic ring, and together with $R^2$ form a —$(CH_2)_n$— bridge, wherein n is 1, 2 or 3; and the remaining of $R^3$, $R^4$ and $R^5$, are as defined above;

$R^6$ and $R^7$, independently of each other, represent hydrogen, alkyl, cycloalkyl, halo, haloalkyl, hydroxy, alkoxy, haloalkoxy, amino, alkyl-carbonyl-amino, nitro, cyano or phenyl; and R' and R", independently of each other, represent alkyl, hydroxy-alkyl, amino-alkyl, cycloalkyl, phenyl-alkyl, phenyl-hydroxyalkyl, N-alkyl-amino-alkyl, N,N-dialkyl-amino-alkyl, alkoxy-alkyl, phenyl-alkyl, piperidinyl, N-alkyl-piperidinyl, furanyl-alkyl, pyridinyl-alkyl, pyrazolyl-alkyl, imidazolyl-alkyl, pyrimidinyl, pyrimidinyl substituted with one or two substituents selected from N-alkyl-amino, N,N-dialkyl-amino and phenyl; or R' and R", together with the nitrogen to which they are attached, form a heterocyclic ring selected from pyrrolidinyl, 2,5-dihydro-1H-pyrrol-1-yl, thiazolidinyl, piperidinyl, piperazinyl, homopiperazinyl, morpholinyl and homomorpholinyl, which pyrrolidinyl, piperidinyl, piperazinyl, homopiperazinyl, morpholinyl and homomorpholinyl is optionally substituted one or more times with a substituent selected from the group consisting of alkyl, alkoxy, alkoxy-alkyl, alkyl-carbonyl-amino, cycloalkyl-carbonyl-amino, hydroxy-alkyl, hydroxy, amino, N-alkyl-amino, N,N-dialkyl-amino, amino-alkyl, N-alkyl-amino-alkyl, N,N-dialkyl-amino-alkyl, carbamoyl-alkyl, N-alkyl-carbamoyl-alkyl, N,N-dialkyl-carbamoyl-alkyl, N-hydroxy-alkyl-carbamoyl, N,N-dialkyl-amino-alkyl-carbamoyl, alkoxy-carbonyl, cyano-alkyl, pyrrolidinyl, pyrrolidinyl-alkyl, piperidinyl, piperidinyl-alkyl, piperidinyl-carbonyl, hydroxy-piperidinyl, hydroxy-piperidinyl-alkyl, hydroxy-piperidinyl-carbonyl, piperazinyl, piperidinyl, N-alkyl-piperidinyl, piperidinyl-alkyl, N-alkyl-piperidinyl-alkyl, morpholino-alkyl, morpholino-alkyl-carbamoyl, morpholino-carbonyl-alkyl, triazolyl-alkyl, piperazinyl, piperazinyl-alkyl, piperazinyl-carbonyl, N-alkyl-piperazinyl, N-alkyl-piperazinyl-alkyl, N-alkyl-piperazinyl-carbonyl, pyridinyl, pyridinyl-alkyl, and pyridinyl substituted once or twice with alkyl, trifluoromethyl and/or cyano.

In another aspect the invention provides pharmaceutical compositions comprising a therapeutically effective amount of the 2,3-diamino-quinazolinone derivative of the invention, or a pharmaceutically-acceptable addition salt thereof.

In another aspect the invention relates to the use of the 2,3-diamino-quinazolinone derivative of the invention, or a pharmaceutically-acceptable addition salt thereof, for the manufacture of pharmaceutical compositions.

In another aspect the invention provides a method of treatment, prevention or alleviation of a disease or a disorder or a condition of a living animal body, including a human, which disorder, disease or condition is responsive to activation of $K_v7$ channels, which method comprises the step of administering to such a living animal body in need thereof, a therapeutically effective amount of the 2,3-diamino-quinazolinone derivative of the invention, or a pharmaceutically-acceptable addition salt thereof.

Other objects of the invention will be apparent to the person skilled in the art from the following detailed description and examples.

DETAILED DISCLOSURE OF THE INVENTION

The 2,3-diamino-quinazolinone derivatives of the invention may be characterised by Formula (I)

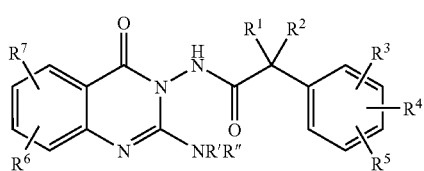

(I)

a stereoisomer or a mixture of its stereoisomers, or a pharmaceutically-acceptable addition salt thereof, or an N-oxide thereof, wherein
$R^1$ represents hydrogen, alkyl or halo; and
$R^2$ represents hydrogen, alkyl, cycloalkyl, halo, haloalkyl, hydroxyalkyl, hydroxy, alkoxy, phenyl, phenyl-alkyl, amino, alkyl-carbonyl-amino, cyano or nitro; or
$R^1$ and $R^2$ together with the carbon atom to which they are attached form a cycloalkyl (spiro) group; or
$R^1$ represents hydrogen; and
$R^2$ together with one of $R^3$, $R^4$ and $R^5$, attached in ortho-position on the aromatic ring, form a —$(CH_2)_n$— bridge, wherein n is 1, 2 or 3;
$R^3$, $R^4$ and $R^5$, independently of each other, represent hydrogen, alkyl, cycloalkyl, halo, haloalkyl, hydroxy, alkoxy, haloalkoxy, amino, alkyl-carbonyl-amino, alkyl-sulfanyl, alkyl-sulfonyl, phenyl, phenoxy, benzoyl, cyano or nitro; or
two of $R^3$, $R^4$ and $R^5$, together form a methylenedioxy group; and the remaining of $R^3$, $R^4$ and $R^5$ is as defined above; or
two of $R^3$, $R^4$ and $R^5$, together with the phenyl group to which they are attached, form a naphthyl group; and the remaining of $R^3$, $R^4$ and $R^5$ is as defined above, or one of $R^3$, $R^4$ and $R^5$, attached in ortho-position on the aromatic ring, and together with $R^2$ form a —$(CH_2)_n$— bridge, wherein n is 1, 2 or 3; and the remaining of $R^3$, $R^4$ and $R^5$, are as defined above;
$R^6$ and $R^7$, independently of each other, represent hydrogen, alkyl, cycloalkyl, halo, haloalkyl, hydroxy, alkoxy, haloalkoxy, amino, alkyl-carbonyl-amino, nitro, cyano or phenyl; and
R' and R", independently of each other, represent alkyl, hydroxy-alkyl, amino-alkyl, cycloalkyl, phenyl-alkyl, phenyl-hydroxyalkyl, N-alkyl-amino-alkyl, N,N-dialkyl-amino-alkyl, alkoxy-alkyl, phenyl-alkyl, piperidinyl, N-alkyl-piperidinyl, furanyl-alkyl, pyridinyl-alkyl, pyrazolyl-alkyl, imidazolyl-alkyl, pyrimidinyl, pyrimidinyl substituted with one or two substituents selected from N-alkyl-amino, N,N-dialkyl-amino and phenyl; or
R' and R", together with the nitrogen to which they are attached, form a heterocyclic ring selected from pyrrolidinyl, 2,5-dihydro-1H-pyrrol-1-yl, thiazolidinyl, piperidinyl, piperazinyl, homopiperazinyl, morpholinyl and homomorpholinyl, which pyrrolidinyl, piperidinyl, piperazinyl, homopiperazinyl, morpholinyl and homomorpholinyl is optionally substituted one or more times with a substituent selected from the group consisting of alkyl, alkoxy, alkoxy-alkyl, alkyl-carbonyl-amino, cycloalkyl-carbonyl-amino, hydroxy-alkyl, hydroxy, amino, N-alkyl-amino, N,N-dialkyl-amino, amino-alkyl, N-alkyl-amino-alkyl, N,N-dialkyl-amino-alkyl, carbamoyl-alkyl, N-alkyl-carbamoyl-alkyl, N,N-dialkyl-carbamoyl-alkyl, N-hydroxy-alkyl-carbamoyl, N,N-dialkyl-amino-alkyl-carbamoyl, alkoxy-carbonyl, cyano-alkyl, pyrrolidinyl, pyrrolidinyl-alkyl, piperidinyl, piperidinyl-alkyl, piperidinyl-carbonyl, hydroxy-piperidinyl, hydroxy-piperidinyl-alkyl, hydroxy-piperidinyl-carbonyl, piperazinyl, piperidinyl, N-alkyl-piperidinyl, piperidinyl-alkyl, N-alkyl-piperidinyl-alkyl, morpholino-alkyl, morpholino-alkyl-carbamoyl, morpholino-carbonyl-alkyl, triazolyl-alkyl, piperazinyl, piperazinyl-alkyl, piperazinyl-carbonyl, N-alkyl-piperazinyl, N-alkyl-piperazinyl-alkyl, N-alkyl-piperazinyl-carbonyl, pyridinyl, pyridinyl-alkyl, and pyridinyl substituted once or twice with alkyl, trifluoromethyl and/or cyano.

In another embodiment, the 2,3-diamino-quinazolinone derivative of the invention is a compound of Formula (I), a stereoisomer or a mixture of its stereo-isomers, or a pharmaceutically-acceptable addition salt thereof, or an N-oxide thereof, wherein
$R^1$ represents hydrogen, alkyl or halo; and
$R^2$ represents hydrogen, alkyl, cycloalkyl, halo, haloalkyl, hydroxyalkyl, hydroxy, alkoxy, phenyl, phenyl-alkyl, amino, alkyl-carbonyl-amino, cyano or nitro; or
$R^1$ and $R^2$ together with the carbon atom to which they are attached form a cycloalkyl (spiro) group; or
$R^1$ represents hydrogen; and
$R^2$ together with one of $R^3$, $R^4$ and $R^5$, attached in ortho-position on the aromatic ring, form a —$(CH_2)_n$— bridge, wherein n is 1, 2 or 3;
$R^3$, $R^4$ and $R^5$, independently of each other, represent hydrogen, alkyl, cycloalkyl, halo, haloalkyl, hydroxy, alkoxy, haloalkoxy, amino, alkyl-carbonyl-amino, alkyl-sulfonyl, phenyl, benzoyl, cyano or nitro; or
two of $R^3$, $R^4$ and $R^5$, together form a methylenedioxy group; and the remaining of $R^3$, $R^4$ and $R^5$ is as defined above; or
one of $R^3$, $R^4$ and $R^5$, attached in ortho-position on the aromatic ring, and together with $R^2$ form a —$(CH_2)_n$— bridge, wherein n is 1, 2 or 3; and the remaining of $R^3$, $R^4$ and $R^5$, are as defined above;
$R^6$ and $R^7$, independently of each other, represent hydrogen, alkyl, cycloalkyl, halo, haloalkyl, hydroxy, alkoxy, haloalkoxy, amino, alkyl-carbonyl-amino, nitro, cyano or phenyl; and R' and R", independently of each other, represent alkyl, hydroxy-alkyl, amino-alkyl, phenyl-alkyl, phenyl-hydroxyalkyl, N-alkyl-amino-alkyl, N,N-dialkyl-amino-alkyl, alkoxy-alkyl, phenyl-alkyl, piperidinyl, N-alkyl-piperidinyl, furanyl-alkyl, pyridinyl-alkyl, pyrazolyl-alkyl, imidazolyl-alkyl, pyrimidinyl, pyrimidinyl substituted with one or two substituents selected from N-alkyl-amino, N,N-dialkyl-amino and phenyl; or R' and R", together with the nitrogen to which they are attached, form a heterocyclic ring selected from pyrrolidinyl, 2,5-dihydro-1H-pyrrol-1-yl, thiazolidinyl, piperidinyl, piperazinyl, homopiperazinyl and morpholinyl, which pyrrolidinyl, piperidinyl, piperazinyl, homopiperazinyl and morpholinyl is optionally substituted one or more times with a substituent selected from the group consisting of alkyl, alkoxy, alkoxy-alkyl, alkyl-carbonyl-amino, cycloalkyl-carbonyl-amino, hydroxy-alkyl, hydroxy, amino, N-alkyl-amino, N,N-dialkyl-amino, amino-alkyl, N-alkyl-amino-alkyl, N,N-dialkyl-amino-alkyl, carbamoyl-alkyl, N-alkyl-carbamoyl-alkyl, N,N-dialkyl-carbamoyl-alkyl, N-hydroxy-alkyl-carbamoyl, N,N-dialkyl-amino-alkyl-carbamoyl, alkoxy-carbonyl, cyano-alkyl, pyrrolidinyl, pyrrolidinyl-alkyl, piperidinyl, piperidinyl-alkyl, piperidinyl-carbonyl, hydroxy-piperidinyl, hydroxy-piperidinyl-alkyl, hydroxy-piperidinyl-carbonyl, piperazinyl, piperidinyl, N-alkyl-piperidinyl, piperidinyl-alkyl, N-alkyl-piperidinyl-alkyl, morpholino-alkyl, morpholino-alkyl-carbamoyl, morpholino-carbonyl-alkyl, triazolyl-alkyl, piperazinyl, piperazinyl-alkyl, piperazinyl-carbonyl, N-alkyl-piperazinyl, N-alkyl-piperazinyl-alkyl, N-alkyl-piperazinyl-carbonyl, pyridinyl, pyridinyl-alkyl, and pyridinyl substituted once or twice with alkyl, trifluoromethyl and/or cyano.

In another embodiment the 2,3-diamino-quinazolinone derivative of the invention is a compound of Formula (I), or a pharmaceutically-acceptable addition salt thereof, or an N-oxide thereof, wherein $R^1$ represents hydrogen or alkyl; and
$R^2$ represents hydrogen or alkyl;
$R^3$, $R^4$ and $R^5$, independently of each other, represent hydrogen, alkyl, halo, haloalkyl, alkoxy, alkyl-sulfanyl, alkyl-sulfonyl, phenyl or phenoxy; or
two of $R^3$, $R^4$ and $R^5$, together form a methylenedioxy group and the remaining of $R^3$, $R^4$ and $R^5$ is as defined above; or
two of $R^3$, $R^4$ and $R^5$, together with the phenyl group to which they are attached, form a naphthyl group and the remaining of $R^3$, $R^4$ and $R^5$ is as defined above;
$R^6$ and $R^7$, independently of each other, represent hydrogen, halo, haloalkyl, hydroxy, alkoxy or amino;
R' and R", independently of each other, represent alkyl, hydroxy-alkyl, cycloalkyl, or phenyl-alkyl, or
R' and R", together with the nitrogen to which they are attached, form a heterocyclic ring selected from pyrrolidinyl, thiazolidinyl, piperidinyl, piperazinyl, homopiperazinyl and morpholinyl, which piperazinyl is optionally substituted with one time with alkyl.

In another embodiment the 2,3-diamino-quinazolinone derivative of the invention is a compound of Formula (I), or a pharmaceutically-acceptable addition salt thereof, or an N-oxide thereof, wherein $R^1$ represents hydrogen or alkyl; and
$R^2$ represents hydrogen or alkyl;
$R^3$, $R^4$ and $R^5$, independently of each other, represent hydrogen, alkyl, halo, haloalkyl, alkoxy, alkyl-sulfonyl, or phenyl;
two of $R^3$, $R^4$ and $R^5$, together form a methylenedioxy group and the remaining of $R^3$, $R^4$ and $R^5$ is as defined above;
$R^6$ and $R^7$, independently of each other, represent hydrogen, halo, haloalkyl, hydroxy, alkoxy, or amino;

R' and R", independently of each other, represent alkyl, hydroxy-alkyl, or phenyl-alkyl; or
R' and R", together with the nitrogen to which they are attached, form a heterocyclic ring selected from pyrrolidinyl, thiazolidinyl, piperidinyl, piperazinyl, homopiperazinyl and morpholinyl, which piperazinyl is optionally substituted with one time with alkyl.

In another embodiment the 2,3-diamino-quinazolinone derivative of the invention is a compound of Formula (Ia)

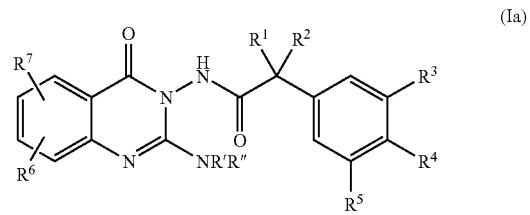

a stereoisomer or a mixture of its stereoisomers, or a pharmaceutically-acceptable addition salt thereof, or an N-oxide thereof, wherein $R^1$, $R^2$, $R^3$, $R^4$, $R^5$, $R^6$, $R^7$, R' and R" are as defined above.

In another embodiment the 2,3-diamino-quinazolinone derivative of the invention is a compound of Formula (Ib)

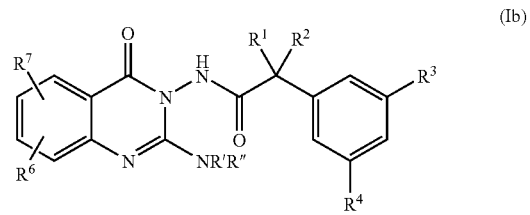

a stereoisomer or a mixture of its stereoisomers, or a pharmaceutically-acceptable addition salt thereof, or an N-oxide thereof, wherein $R^1$, $R^2$, $R^3$, $R^4$, $R^6$, $R^7$, R' and R" are as defined above, (i.e. $R^5$ represents hydrogen).

In another embodiment the 2,3-diamino-quinazolinone derivative of the invention is a compound of Formula (Ic)

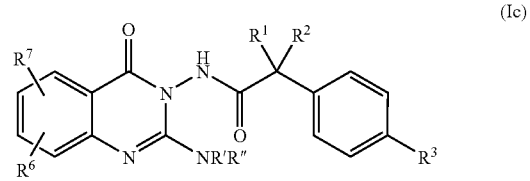

a stereoisomer or a mixture of its stereoisomers, or a pharmaceutically-acceptable addition salt thereof, or an N-oxide thereof, wherein $R^1$, $R^2$, $R^3$, $R^6$, $R^7$, R' and R" are as defined above (i.e. $R^4$ and $R^5$ both represent hydrogen).

In another embodiment the 2,3-diamino-quinazolinone derivative of the invention is a compound of Formula (Id)

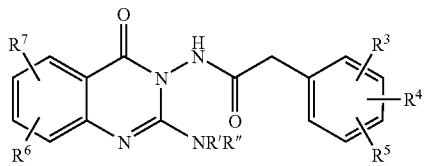

a stereoisomer or a mixture of its stereoisomers, or a pharmaceutically-acceptable addition salt thereof, or an N-oxide thereof, wherein $R^3$, $R^4$, $R^5$, $R^6$, $R^7$, R' and R" are as defined above (i.e. $R^1$ and $R^2$ both represent hydrogen).

In another embodiment the 2,3-diamino-quinazolinone derivative of the invention is a compound of Formula (Ie)

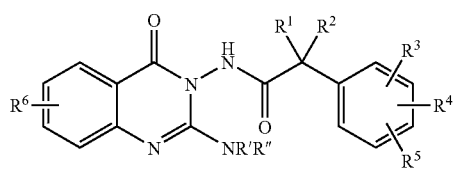

a stereoisomer or a mixture of its stereoisomers, or a pharmaceutically-acceptable addition salt thereof, or an N-oxide thereof, wherein $R^1$, $R^2$, $R^3$, $R^4$, $R^5$, $R^6$, R' and R" are as defined above (i.e. $R^7$ represents hydrogen).

In another embodiment the 2,3-diamino-quinazolinone derivative of the invention is a compound of Formula (If)

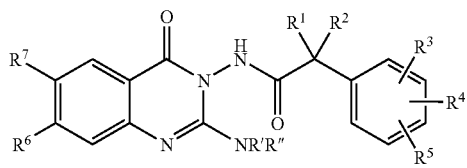

a stereoisomer or a mixture of its stereoisomers, or a pharmaceutically-acceptable addition salt thereof, or an N-oxide thereof, wherein $R^1$, $R^2$, $R^3$, $R^4$, $R^5$, $R^6$, $R^7$, R' and R" are as defined above.

In another embodiment the 2,3-diamino-quinazolinone derivative of the invention is a compound of Formula (Ig)

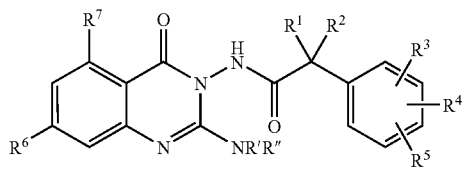

a stereoisomer or a mixture of its stereoisomers, or a pharmaceutically-acceptable addition salt thereof, or an N-oxide thereof, wherein $R^1$, $R^2$, $R^3$, $R^4$, $R^5$, $R^6$, $R^7$, R' and R" are as defined above.

In another embodiment the 2,3-diamino-quinazolinone derivative of the invention is a compound of Formula (Ia), (Ib) or (Ic), or a pharmaceutically-acceptable addition salt thereof, or an N-oxide thereof, wherein $R^1$ represents hydrogen, alkyl or halo; and $R^2$ represents hydrogen, alkyl, cycloalkyl, halo, haloalkyl, hydroxyalkyl, hydroxy, alkoxy, phenyl, phenyl-alkyl, amino, alkyl-carbonyl-amino, cyano or nitro.

In another embodiment the 2,3-diamino-quinazolinone derivative of the invention is a compound of Formula (Ie), or a pharmaceutically-acceptable addition salt thereof, or an N-oxide thereof, wherein $R^1$ represents hydrogen, alkyl or halo; and $R^2$ represents hydrogen, alkyl, cycloalkyl, halo, haloalkyl, hydroxyalkyl, hydroxy, alkoxy, phenyl, phenyl-alkyl, amino, alkyl-carbonyl-amino, cyano or nitro.

In another embodiment the 2,3-diamino-quinazolinone derivative of the invention is a compound of Formula (If) or (Ig), or a pharmaceutically-acceptable addition salt thereof, or an N-oxide thereof, wherein $R^1$ represents hydrogen, alkyl or halo; and $R^2$ represents hydrogen, alkyl, cycloalkyl, halo, haloalkyl, hydroxyalkyl, hydroxy, alkoxy, phenyl, phenyl-alkyl, amino, alkyl-carbonyl-amino, cyano or nitro.

In another embodiment the 2,3-diamino-quinazolinone derivative of the invention is a compound of Formula (I), (Ia), (Ib), (Ic), (Ie), (If) or (Ig), or a pharmaceutically-acceptable addition salt thereof, or an N-oxide thereof, wherein $R^1$ represents hydrogen or alkyl; and $R^2$ represents hydrogen or alkyl.

In another embodiment the 2,3-diamino-quinazolinone derivative of the invention is a compound of Formula (I), (Ia), (Ib), (Ic), (Ie), (If) or (Ig), or a pharmaceutically-acceptable addition salt thereof, or an N-oxide thereof, wherein $R^1$ represents hydrogen and $R^2$ represents hydrogen.

In another embodiment $R^1$ represents hydrogen, alkyl or halo.

In another embodiment $R^1$ represents hydrogen or alkyl.

In another embodiment $R^1$ represents hydrogen.

In another embodiment $R^1$ represents alkyl.

In another embodiment $R^1$ represents alkyl, and in particular methyl.

In another embodiment $R^1$ represents halo, an in particular fluoro.

In another embodiment $R^2$ represents hydrogen or alkyl.

In another embodiment $R^2$ represents hydrogen.

In another embodiment $R^2$ represents alkyl, and in particular methyl.

In another embodiment $R^1$ represents hydrogen and $R^2$ represents hydrogen.

In another embodiment the 2,3-diamino-quinazolinone derivative of the invention is a compound of Formula (Ia), (Ib) or (Ic), or a pharmaceutically-acceptable addition salt thereof, or an N-oxide thereof, wherein $R^1$ and $R^2$ together with the carbon atom to which they are attached form a cycloalkyl (spiro) group.

In another embodiment the 2,3-diamino-quinazolinone derivative of the invention is a compound of Formula (Ia), (Ib) or (Ic), or a pharmaceutically-acceptable addition salt thereof, or an N-oxide thereof, wherein $R^1$ represents hydrogen; and $R^2$ together with one of $R^3$, $R^4$ and $R^5$, attached in ortho-position on the aromatic ring, form a —$(CH_2)_n$— bridge, wherein n is 1, 2 or 3.

In another embodiment the 2,3-diamino-quinazolinone derivative of the invention is a compound of Formula (Ia), or a pharmaceutically-acceptable addition salt thereof, or an N-oxide thereof, wherein $R^3$, $R^4$ and $R^5$, independently of each other, represent hydrogen, alkyl, cycloalkyl, halo, haloalkyl, hydroxy, alkoxy, haloalkoxy, amino, alkyl-carbonyl-amino, alkyl-sulfonyl, phenyl, benzoyl, cyano or nitro.

In another embodiment the 2,3-diamino-quinazolinone derivative of the invention is a compound of Formula (Ib), or a pharmaceutically-acceptable addition salt thereof, or an N-oxide thereof, wherein $R^3$ and $R^4$, independently of each other, represent hydrogen, alkyl, cycloalkyl, halo, haloalkyl, alkoxy, haloalkoxy, amino, alkyl-carbonyl-amino, alkyl-sulfonyl, phenyl, benzoyl, cyano or nitro.

In another embodiment the 2,3-diamino-quinazolinone derivative of the invention is a compound of Formula (Ib), or a pharmaceutically-acceptable addition salt thereof, or an N-oxide thereof, wherein $R^3$ and $R^4$ independently of each other, represent halo or haloalkyl.

In another embodiment the 2,3-diamino-quinazolinone derivative of the invention is a compound of Formula (Ib), or a pharmaceutically-acceptable addition salt thereof, or an N-oxide thereof, wherein $R^3$ and $R^4$ both represent halo.

In another embodiment the 2,3-diamino-quinazolinone derivative of the invention is a compound of Formula (Ic), or a pharmaceutically-acceptable addition salt thereof, or an N-oxide thereof, wherein $R^3$ represents hydrogen, alkyl, cycloalkyl, halo, halo-alkyl, alkoxy, haloalkoxy, amino, alkyl-carbonyl-amino, alkyl-sulfanyl, alkyl-sulfonyl, phenyl, phenoxy, benzoyl, cyano or nitro.

In another embodiment the 2,3-diamino-quinazolinone derivative of the invention is a compound of Formula (Ic), or a pharmaceutically-acceptable addition salt thereof, or an N-oxide thereof, wherein $R^3$ represents hydrogen, alkyl, halo, haloalkyl, alkoxy, amino, alkyl-carbonyl-amino, alkyl-sulfanyl, alkyl-sulfonyl, phenyl, or phenoxy.

In another embodiment the 2,3-diamino-quinazolinone derivative of the invention is a compound of Formula (Ic), or a pharmaceutically-acceptable addition salt thereof, or an N-oxide thereof, wherein $R^3$ represents halo.

In another embodiment the 2,3-diamino-quinazolinone derivative of the invention is a compound of Formula (Id), (Ie), (If) or (Ig), or a pharmaceutically-acceptable addition salt thereof, or an N-oxide thereof, wherein $R^3$, $R^4$ and $R^5$, independently of each other, represent hydrogen, alkyl, cycloalkyl, halo, haloalkyl, alkoxy, haloalkoxy, amino, alkyl-carbonyl-amino, alkyl-sulfanyl, alkyl-sulfonyl, phenyl, phenoxy, benzoyl, cyano or nitro.

In another embodiment $R^3$, $R^4$ and $R^5$, independently of each other, represent hydrogen, halo, trifluoromethyl, alkoxy or alkyl-sulfonyl.

In another embodiment one of $R^3$, $R^4$ and $R^5$ represents halo, trifluoromethyl, alkyl-sulfonyl or alkoxy; and the others of $R^3$, $R^4$ and $R^5$ represent hydrogen.

In another embodiment all of $R^3$, $R^4$ and $R^5$ represent hydrogen.

In another embodiment one of $R^3$, $R^4$ and $R^5$ represent alkyl; and the remaining of $R^3$, $R^4$ and $R^5$ represents hydrogen.

In another embodiment one of $R^3$, $R^4$ and $R^5$ represents halo, and in particular chloro; and the others of $R^3$, $R^4$ and $R^5$ represent hydrogen.

In another embodiment one of $R^3$, $R^4$ and $R^5$ represents trifluoromethyl; and the others of $R^3$, $R^4$ and $R^5$ represent hydrogen.

In another embodiment one of $R^3$, $R^4$ and $R^5$ represents alkyl-sulfonyl, and in particular methyl-sulfonyl; and the others of $R^3$, $R^4$ and $R^5$ represent hydrogen.

In another embodiment one of $R^3$, $R^4$ and $R^5$ represents alkyl-sulfanyl, and the remaining of $R^3$, $R^4$ and $R^5$ represent hydrogen.

In another embodiment one of $R^3$, $R^4$ and $R^5$ represents phenyl, and the remaining of $R^3$, $R^4$ and $R^5$ represent hydrogen.

In another embodiment one of $R^3$, $R^4$ and $R^5$ represents phenoxy, and the remaining of $R^3$, $R^4$ and $R^5$ represent hydrogen.

In another embodiment one of $R^3$, $R^4$ and $R^5$ represents alkoxy, and in particular butoxy; and the others of $R^3$, $R^4$ and $R^5$ represent hydrogen.

In another embodiment two of $R^3$, $R^4$ and $R^5$ represent halo, and in particular fluoro, or trifluoromethyl; and the remaining of $R^3$, $R^4$ and $R^5$ represents hydrogen.

In another embodiment two of $R^3$, $R^4$ and $R^5$ represent halo, and in particular fluoro; and the remaining of $R^3$, $R^4$ and $R^5$ represents hydrogen.

In another embodiment two of $R^3$, $R^4$ and $R^5$ represent trifluoromethyl; and the remaining of $R^3$, $R^4$ and $R^5$ represents hydrogen.

In another embodiment the 2,3-diamino-quinazolinone derivative of the invention is a compound of Formula (Ia), or a pharmaceutically-acceptable addition salt thereof, or an N-oxide thereof, wherein two of $R^3$, $R^4$ and $R^5$, together form a methylenedioxy group; and the remaining of $R^3$, $R^4$ and $R^5$ is as defined above.

In another embodiment two of $R^3$, $R^4$ and $R^5$, together form a methylenedioxy group; and the remaining of $R^3$, $R^4$ and $R^5$ is hydrogen.

In another embodiment the 2,3-diamino-quinazolinone derivative of the invention is a compound of Formula (Ia), or a pharmaceutically-acceptable addition salt thereof, or an N-oxide thereof, wherein one of $R^3$, $R^4$ and $R^5$, attached in ortho-position on the aromatic ring, and together with $R^2$ form a —$(CH_2)_n$— bridge, wherein n is 1, 2 or 3; and the remaining of $R^3$, $R^4$ and $R^5$, are as defined above.

In another embodiment the 2,3-diamino-quinazolinone derivative of the invention is a compound of Formula (I), or a pharmaceutically-acceptable addition salt thereof, or an N-oxide thereof, wherein two of $R^3$, $R^4$ and $R^5$, together with the phenyl group to which they are attached, form a naphthyl group and the remaining of $R^3$, $R^4$ and $R^5$ is as defined above.

In another embodiment the 2,3-diamino-quinazolinone derivative of the invention is a compound of Formula (Ia), (Id), (Ie), (If) or (Ig), or a pharmaceutically-acceptable addition salt thereof, or an N-oxide thereof, wherein two of $R^3$, $R^4$ and $R^5$, together with the phenyl group to which they are attached, form a naphthyl group and the remaining of $R^3$, $R^4$ and $R^5$ is as defined above.

In another embodiment the 2,3-diamino-quinazolinone derivative of the invention is a compound of Formula (Ia), (Ib) or (Ic), or a pharmaceutically-acceptable addition salt thereof, or an N-oxide thereof, wherein $R^6$ and $R^7$, independently of each other, represent hydrogen, alkyl, cycloalkyl, halo, haloalkyl, hydroxy, alkoxy, haloalkoxy, amino, alkyl-carbonyl-amino (and in particular acetamido), nitro, cyano or phenyl.

In another embodiment the 2,3-diamino-quinazolinone derivative of the invention is a compound of Formula (I), (Ia), (Ib) or (Ic), or a pharmaceutically-acceptable addition salt thereof, or an N-oxide thereof, wherein $R^6$ and $R^7$, independently of each other, represent hydrogen, halo, haloalkyl, hydroxy, alkoxy, or amino.

In another embodiment the 2,3-diamino-quinazolinone derivative of the invention is a compound of Formula (Ie), or a pharmaceutically-acceptable addition salt thereof, or an N-oxide thereof, wherein $R^6$ represents hydrogen, alkyl, cycloalkyl, halo, halo-alkyl, hydroxy, alkoxy, haloalkoxy, amino, alkyl-carbonyl-amino (and in particular acetamido), nitro, cyano or phenyl.

In another embodiment the 2,3-diamino-quinazolinone derivative of the invention is a compound of Formula (Ie), or a pharmaceutically-acceptable addition salt thereof, or an N-oxide thereof, wherein $R^6$ represents hydrogen, halo, haloalkyl, hydroxy, alkoxy, or amino.

In another embodiment the 2,3-diamino-quinazolinone derivative of the invention is a compound of Formula (Id), (If) or (Ig), or a pharmaceutically-acceptable addition salt thereof, or an N-oxide thereof, wherein $R^6$ and $R^7$, independently of each other, represent hydrogen, alkyl, cycloalkyl, halo, haloalkyl, hydroxy, alkoxy, haloalkoxy, amino, alkyl-carbonyl-amino (and in particular acetamido), nitro, cyano or phenyl.

In another embodiment the 2,3-diamino-quinazolinone derivative of the invention is a compound of Formula (Id), (If) or (Ig), or a pharmaceutically-acceptable addition salt thereof, or an N-oxide thereof, wherein $R^6$ and $R^7$, independently of each other, represent hydrogen, halo, haloalkyl, hydroxy, alkoxy, or amino.

In another embodiment $R^6$ and $R^7$, independently of each other, represent hydrogen and/or trifluoromethyl.

In another embodiment one of $R^6$ and $R^7$ represents hydrogen; and the other of $R^6$ and $R^7$ represents trifluoromethyl.

In another embodiment one of $R^6$ and $R^7$ represents hydrogen; and the other of $R^6$ and $R^7$ represents halo.

In another embodiment one of $R^6$ and $R^7$ represents hydrogen; and the other of $R^6$ and $R^7$ represents trifluoromethyl.

In another embodiment one of $R^6$ and $R^7$ represents hydrogen; and the other of $R^6$ and $R^7$ represents alkoxy.

In another embodiment one of $R^6$ and $R^7$ represents hydrogen; and the other of $R^6$ and $R^7$ represents hydroxy.

In another embodiment one of $R^6$ and $R^7$ represents hydrogen; and the other of $R^6$ and $R^7$ represents amino.

In another embodiment $R^6$ and $R^7$ both represent hydrogen.

In another embodiment $R^6$ and $R^7$ both represent trifluoromethyl.

In another embodiment $R^6$ and $R^7$ both represent halo.

In another embodiment the 2,3-diamino-quinazolinone derivative of the invention is a compound of Formula (I), (Ia), (Ib) or (Ic), or a pharmaceutically-acceptable addition salt thereof, or an N-oxide thereof, wherein R' and R", independently of each other, represent alkyl, hydroxy-alkyl, amino-alkyl, cycloalkyl, phenyl-alkyl, phenyl-hydroxyalkyl, N-alkyl-amino-alkyl, N,N-dialkyl-amino-alkyl, alkoxy-alkyl, phenyl-alkyl, piperidinyl, N-alkyl-piperidinyl, furanyl-alkyl, pyridinyl-alkyl, pyrazolyl-alkyl, imidazolyl-alkyl, pyrimidinyl, pyrimidinyl substituted with one or two substituents selected from N-alkyl-amino, N,N-dialkyl-amino and phenyl.

In another embodiment the 2,3-diamino-quinazolinone derivative of the invention is a compound of Formula (Id), (Ie), (If) or (Ig), or a pharmaceutically-acceptable addition salt thereof, or an N-oxide thereof, wherein R' and R", independently of each other, represent alkyl, hydroxy-alkyl, amino-alkyl, cycloalkyl, phenyl-alkyl, phenyl-hydroxyalkyl, N-alkyl-amino-alkyl, N,N-dialkyl-amino-alkyl, alkoxy-alkyl, phenyl-alkyl, piperidinyl, N-alkyl-piperidinyl, furanyl-alkyl, pyridinyl-alkyl, pyrazolyl-alkyl, imidazolyl-alkyl, pyrimidinyl, pyrimidinyl substituted with one or two substituents selected from N-alkyl-amino, N,N-dialkyl-amino and phenyl.

In another embodiment the 2,3-diamino-quinazolinone derivative of the invention is a compound of Formula (I), (Ia), (Ib), (Ic), (Id), (Ie), (If) or (Ig), or a pharmaceutically-acceptable addition salt thereof, or an N-oxide thereof, wherein R' and R", independently of each other, represent alkyl, hydroxy-alkyl, cycloalkyl or phenyl-alkyl.

In another embodiment the 2,3-diamino-quinazolinone derivative of the invention is a compound of Formula (I), (Ia), (Ib), (Ic), (Id), (Ie), (If) or (Ig), or a pharmaceutically-acceptable addition salt thereof, or an N-oxide thereof, wherein R' and R" both represent alkyl.

In another embodiment R' and R", independently of each other, represent alkyl or cycloalkyl.

In another embodiment R' and R", independently of each other, represent alkyl, alkoxy-alkyl or phenyl-alkyl.

In another embodiment R' represents alkyl; and R" represents alkyl, alkoxy-alkyl or phenyl-alkyl.

In another embodiment R' represents alkyl; and R" represents alkoxy-alkyl.

In another embodiment R' represents alkyl, in particular methyl or ethyl; and R" represents alkyl, in particular methyl or ethyl.

In another embodiment R' represents alkyl, and in particular methyl or ethyl; and R" represents alkoxy-alkyl, in particular methoxy-ethyl, or phenyl-alkyl, in particular benzyl.

In another embodiment R' and R" both represent alkyl, and in particular methyl or ethyl.

In another embodiment R' represents methyl; and R" represents ethyl.

In another embodiment R' and R" both represent methyl.

In another embodiment R' and R" both represent ethyl.

In another embodiment the 2,3-diamino-quinazolinone derivative of the invention is a compound of Formula (I), (Ia), (Ib) or (Ic), or a pharmaceutically-acceptable addition salt thereof, or an N-oxide thereof, wherein R' represents alkyl; and R" represents alkyl, amino-alkyl, hydroxy-alkyl, N,N-dialkyl-amino-alkyl, N-alkyl-pyrrolidinyl, pyridinyl-alkyl or N-alkyl-piperidinyl.

In another embodiment R' represents methyl, ethyl, propyl, isopropyl, 1-methyl-propyl, 1-methyl-butyl or 1-methyl-heptyl; and R" represents ethyl, 1-methyl-butyl, 2-amino-ethyl, 2-hydroxy-ethyl, N,N-diethyl-amino-ethyl, N-methyl-pyrrolidin-3-yl, 2-pyridin-4-yl-ethyl or N-methyl-piperidin-4-yl.

In another embodiment the 2,3-diamino-quinazolinone derivative of the invention is a compound of Formula (I), (Ia), (Ib) or (Ic), or a pharmaceutically-acceptable addition salt thereof, or an N-oxide thereof, wherein R' and R", together with the nitrogen to which they are attached, form a heterocyclic ring selected from pyrrolidinyl, 2,5-dihydro-1H-pyrrol-1-yl, thiazolidinyl, piperidinyl, piperazinyl, homopiperazinyl and morpholinyl, which pyrrolidinyl, piperidinyl, piperazinyl, homopiperazinyl and morpholinyl is optionally substituted one or more times with a substituent selected from the group consisting of alkyl, alkoxy, alkoxy-alkyl, alkyl-carbonyl-amino, cycloalkyl-carbonyl-amino, hydroxy-alkyl, hydroxy, amino, N-alkyl-amino, N,N-dialkyl-amino, amino-alkyl, N-alkyl-amino-alkyl, N,N-dialkyl-amino-alkyl, carbamoyl-alkyl, N-alkyl-carbamoyl-alkyl, N,N-dialkyl-carbamoyl-alkyl, N-hydroxy-alkyl-carbamoyl, N,N-dialkyl-amino-alkyl-carbamoyl, alkoxy-carbonyl, cyano-alkyl, pyrrolidinyl, pyrrolidinyl-alkyl, piperidinyl, piperidinyl-alkyl, piperidinyl-carbonyl, hydroxy-piperidinyl, hydroxy-piperidinyl-alkyl, hydroxy-piperidinyl-carbonyl, piperazinyl, piperidinyl, N-alkyl-piperidinyl, piperidinyl-alkyl, N-alkyl-piperidinyl-alkyl, morpholino-alkyl, morpholino-alkyl-carbamoyl, morpholino-carbonyl-alkyl, triazolyl-alkyl, piperazinyl, piperazinyl-alkyl, piperazinyl-carbonyl, N-alkyl-piperazinyl, N-alkyl-piperazinyl-alkyl, N-alkyl-piperazinyl-carbonyl, pyridinyl, pyridinyl-alkyl, and pyridinyl substituted once or twice with alkyl, trifluoro-methyl and/or cyano.

In another embodiment the 2,3-diamino-quinazolinone derivative of the invention is a compound of Formula (Id), (Ie), (If) or (Ig), or a pharmaceutically-acceptable addition salt thereof, or an N-oxide thereof, wherein R' and R", together with the nitrogen to which they are attached, form a heterocyclic ring selected from pyrrolidinyl, 2,5-dihydro-1H-pyrrol-1-yl, thiazolidinyl, piperidinyl, piperazinyl, homopiperazinyl and morpholinyl, which pyrrolidinyl, piperidinyl, piperazinyl, homopiperazinyl, morpholinyl and homomorpholinyl is optionally substituted one or more times with a substituent selected from the group consisting of alkyl, alkoxy, alkoxy-alkyl, alkyl-carbonyl-amino, cycloalkyl-carbonyl-amino, hydroxy-alkyl, hydroxy, amino, N-alkyl-amino, N,N-dialkyl-amino, amino-alkyl, N-alkyl-amino-alkyl, N,N-dialkyl-amino-alkyl, carbamoyl-alkyl, N-alkyl-carbamoyl-alkyl, N,N-dialkyl-carbamoyl-alkyl, N-hydroxy-alkyl-carbamoyl, N,N-dialkyl-amino-alkyl-carbamoyl, alkoxy-carbonyl, cyano-alkyl, pyrrolidinyl, pyrrolidinyl-alkyl, piperidinyl, piperidinyl-alkyl, piperidinyl-carbonyl, hydroxy-piperidinyl, hydroxy-piperidinyl-alkyl, hydroxy-piperidinyl-carbonyl, piperazinyl, piperidinyl, N-alkyl-piperidinyl, piperidinyl-alkyl, N-alkyl-piperidinyl-alkyl, morpholino-alkyl, morpholino-alkyl-carbamoyl, morpholino-carbonyl-alkyl, triazolyl-alkyl, piperazinyl, piperazinyl-alkyl, piperazinyl-carbonyl, N-alkyl-piperazinyl, N-alkyl-piperazinyl-alkyl, N-alkyl-piperazinyl-carbonyl, pyridinyl, pyridinyl-alkyl, and pyridinyl substituted once or twice with alkyl, trifluoromethyl and/or cyano.

In another embodiment the 2,3-diamino-quinazolinone derivative of the invention is a compound of Formula (I), (Ia), (Ib), (Ic), (Id), (Ie), (If) or (Ig), or a pharmaceutically-acceptable addition salt thereof, or an N-oxide thereof, wherein R' and R", together with the nitrogen to which they are attached, form a heterocyclic ring selected from pyrrolidinyl, thiazolidinyl, piperidinyl, piperazinyl, homopiperazinyl and morpholinyl, which piperazinyl is optionally substituted with one time with alkyl.

In another embodiment the 2,3-diamino-quinazolinone derivative of the invention is a compound of Formula (I), (Ia), (Ib), (Ic), (Id), (Ie), (If) or (Ig), or a pharmaceutically-acceptable addition salt thereof, or an N-oxide thereof, wherein R' and R", together with the nitrogen to which they are attached, form a heterocyclic ring which is pyrrolidinyl.

In another embodiment the 2,3-diamino-quinazolinone derivative of the invention is a compound of Formula (I), (Ia), (Ib), (Ic), (Id), (Ie), (If) or (Ig), or a pharmaceutically-acceptable addition salt thereof, or an N-oxide thereof, wherein R' and R", together with the nitrogen to which they are attached, form a heterocyclic ring which is thiazolidinyl.

In another embodiment the 2,3-diamino-quinazolinone derivative of the invention is a compound of Formula (I), (Ia), (Ib), (Ic), (Id), (Ie), (If) or (Ig), or a pharmaceutically-acceptable addition salt thereof, or an N-oxide thereof, wherein R' and R", together with the nitrogen to which they are attached, form a heterocyclic ring which is piperidinyl.

In another embodiment the 2,3-diamino-quinazolinone derivative of the invention is a compound of Formula (I), (Ia), (Ib), (Ic), (Id), (Ie), (If) or (Ig), or a pharmaceutically-acceptable addition salt thereof, or an N-oxide thereof, wherein R' and R", together with the nitrogen to which they are attached, form a heterocyclic ring which is piperazinyl is optionally substituted with one time with alkyl.

In another embodiment the 2,3-diamino-quinazolinone derivative of the invention is a compound of Formula (I), (Ia), (Ib), (Ic), (Id), (Ie), (If) or (Ig), or a pharmaceutically-acceptable addition salt thereof, or an N-oxide thereof, wherein R' and R", together with the nitrogen to which they are attached, form a heterocyclic ring which is morpholinyl.

In another embodiment R' and R", together with the nitrogen to which they are attached, form a pyrrolidinyl ring, which pyrrolidinyl is optionally substituted with hydroxy, pyridinyl, N,N-dialkyl-amino or alkyl-carbonyl-amino.

In another embodiment the pyrrolidinyl ring is pyrrolidin-1-yl, 3-hydroxy-pyrrolidin-1-yl, 2-(pyridin-2-yl)-pyrrolidin-1-yl, 2-(pyridin-3-yl)-pyrrolidin-1-yl, 2-(pyridin-4-yl)-pyrrolidin-1-yl, 3-acetamido-pyrrolidin-1-yl, or N,N-dimethyl-amino-pyrrolidin-1-yl.

In another embodiment R' and R", together with the nitrogen to which they are attached, form a 2,5-dihydro-1H-pyrrol-1-yl ring.

In another embodiment R' and R", together with the nitrogen to which they are attached, form a thiazolidinyl ring.

In another embodiment R' and R", together with the nitrogen to which they are attached, form a thiazolidin-3-yl ring.

In another embodiment R' and R", together with the nitrogen to which they are attached, form a piperidinyl ring, which piperidinyl is optionally substituted with pyrrolidinyl, pyrrolidinyl-alkyl, N-alkyl-piperazinyl-carbonyl, hydroxy-piperidinyl-carbonyl, hydroxy-alkyl-carbamoyl, cycloalkyl-carbonyl-amino, N,N-dialkyl-amino-alkyl-carbamoyl, morpholinyl-alkyl-carbamoyl, alkoxy-carbonyl (i.e. an alkyl-ester) or piperazinyl-alkyl.

In another embodiment the piperidinyl ring is 4-(pyrrolidin-1-yl)-piperidin-1-yl, 4-(2-pyrrolidin-1-yl-ethyl)-piperidin-1-yl, 4-(N-methyl-piperazin-1-yl)-carbonyl-piperidin-1-yl, 3-(4-hydroxy-piperidin-1-yl)-carbonyl-piperidin-1-yl, 3-N-(2-hydroxy-ethyl)-carbamoyl-piperidin-1-yl, 3-N-(3-hydroxy-propyl)-carbamoyl-piperidin-1-yl, 4-N-(2-hydroxy-ethyl)-carbamoyl-piperidin-1-yl, 4-(cyclohexyl-carbonyl-amino)-pyrrolidin-1-yl, 3-{N—(N,N-dimethyl-amino)-ethyl}-carbamoyl)-piperidin-1-yl, 4-{N—(N,N-dimethyl-amino)-ethyl}-carbamoyl)-piperidin-1-yl, 3-(t-butoxy-carbonyl)-piperidin-1-yl or 4-(t-butoxy-carbonyl)-piperidin-1-yl.

In another embodiment R' and R", together with the nitrogen to which they are attached, form a piperazinyl ring, which piperazinyl is optionally substituted with hydroxy-alkyl, alkoxy-alkyl, cyano-alkyl, trifluoromethyl-pyridinyl, N,N-dialkyl-amino-alkyl, N,N-dialkyl-amino-carbonyl-alkyl, morpholino-alkyl, morpholino-carbonyl-alkyl, alkyl-pyridinyl, cyano-pyridinyl or pyridinyl-alkyl.

In another embodiment the piperazinyl ring is 4-(2-methoxy-ethyl)-piperazin-1-yl, 4-(3-cyano-propyl)-piperazin-1-yl, 4-(N,N-dimethyl-amino-carbonyl-methyl)-piperazin-1-yl, 4-(3-cyano-pyridin-2-yl)-piperazin-1-yl, 4-(3-trifluoromethyl-pyridin-2-yl)-piperazin-1-yl, 4-(5-trifluoromethyl-pyridin-2-yl)-piperazin-1-yl, 4-(6-trifluoromethyl-pyridin-2-yl)-piperazin-1-yl, 4-(6-methyl-pyridin-2-yl)-piperazin-1-yl, 4-{3-(N,N-dimethyl-amino)-propyl}-piperazin-1-yl, 4-{2-(N,N-dimethyl-amino)-ethyl}piperazin-1-yl, 4-{2-(N,N-diisopropyl-amino)-ethyl}-piperazin-1-yl, 4-{3-(pyrrolidin-3-yl)-propyl}-piperazin-1-yl, 4-{2-(morpholin-4-yl)-ethyl}piperazin-1-yl, 4-(pyridine-4-yl-methyl)piperazin-1-yl, 4-{2-(pyridine-2-yl)-ethyl}-piperazin-1-yl, 4-(morpholin-4-yl-carbonyl-methyl)-piperazin-1-yl or 4-(N-methyl-piperidin-3-yl-methyl)-piperazin-1-yl.

In another embodiment R' and R", together with the nitrogen to which they are attached, form a homopiperazinyl ring, which homopiperazinyl is optionally substituted with pyrrolidinyl-alkyl.

In another embodiment the homopiperazinyl ring is 4-(3-pyrrolidin-1-yl-propyl)-homopiperazin-1-yl.

In another embodiment R' and R", together with the nitrogen to which they are attached, form a heterocyclic ring selected from pyrrolidinyl, 2,5-dihydro-1H-pyrrol-1-yl, thiazolidinyl, piperidinyl, piperazinyl, homopiperazinyl and morpholinyl.

In another embodiment R' and R", together with the nitrogen to which they are attached, form a pyrrolidinyl ring.

In another embodiment R' and R", together with the nitrogen to which they are attached, form a 2,5-dihydro-1H-pyrrol-1-yl ring.

In another embodiment R' and R", together with the nitrogen to which they are attached, form a thiazolidinyl ring.

In another embodiment R' and R", together with the nitrogen to which they are attached, form a piperidinyl ring.

In another embodiment R' and R", together with the nitrogen to which they are attached, form a piperazinyl ring.

In another embodiment R' and R", together with the nitrogen to which they are attached, form a homopiperazinyl ring.

In another embodiment R' and R", together with the nitrogen to which they are attached, form a morpholinyl ring.

In another embodiment R' and R", together with the nitrogen to which they are attached, form a homomorpholinyl ring.

In another embodiment R' and R", together with the nitrogen to which they are attached, form a pyrrolidinyl or thiazolidinyl ring.

In another embodiment the 2,3-diamino-quinazolinone derivative of the invention is:
2-(3,5-Difluoro-phenyl)-N-(4-oxo-2-pyrrolidin-1-yl-4H-quinazolin-3-yl)-acetamide;
2-(3,5-Difluoro-phenyl)-N-(2-dimethylamino-4-oxo-4H-quinazolin-3-yl)-acetamide;
2-(4-Chloro-phenyl)-N-(2-diethylamino-4-oxo-4H-quinazolin-3-yl)-acetamide;
2-(3,5-Difluoro-phenyl)-N-[2-(ethyl-methyl-amino)-4-oxo-4H-quinazolin-3-yl]-acetamide;
2-(3,5-Difluoro-phenyl)-N-(2-dimethylamino-4-oxo-7-trifluoromethyl-4H-quinazolin-3-yl)-propionamide;
N-(2-Diethylamino-4-oxo-4H-quinazolin-3-yl)-2-(4-methanesulfonyl-phenyl)-acetamide;
N-{2-[(2-Methoxy-ethyl)-methyl-amino]-4-oxo-4H-quinazolin-3-yl}-2-(4-trifluoromethyl-phenyl)-acetamide;
2-(4-Butoxy-phenyl)-N-{2-[(2-methoxy-ethyl)-methyl-amino]-4-oxo-4H-quinazolin-3-yl}-acetamide;
N-[2-(Benzyl-methyl-amino)-4-oxo-4H-quinazolin-3-yl]-2-(4-methanesulfonyl-phenyl)-acetamide;
2-(4-Butoxy-phenyl)-N-(4-oxo-2-pyrrolidin-1-yl-4H-quinazolin-3-yl)-acetamide;
2-(3,5-Difluoro-phenyl)-N-(4-oxo-2-thiazolidin-3-yl-4H-quinazolin-3-yl)-acetamide;
N-(2-Diethylamino-4-oxo-4H-quinazolin-3-yl)-2-(3,5-difluoro-phenyl)-acetamide;
2-(3,5-Bis-trifluoromethyl-phenyl)-N-(4-oxo-2-thiazolidin-3-yl-4H-quinazolin-3-yl)-acetamide;
2-Benzo[1,3]dioxol-5-yl-N-(2-diethylamino-4-oxo-4H-quinazolin-3-yl)-acetamide;
N-(2-Diethylamino-4-oxo-4H-quinazolin-3-yl)-2-phenyl-acetamide; or
N-[2-(Ethyl-methyl-amino)-4-oxo-4H-quinazolin-3-yl]-2-phenyl-acetamide; or
a pharmaceutically-acceptable addition salt thereof.

In another embodiment the 2,3-diamino-quinazolinone derivative of the invention is:
2-(3-Fluoro-4-trifluoromethyl-phenyl)-N-(4-oxo-2-pyrrolidin-1-yl-4H-quinazolin-3-yl)-acetamide;
2-(3,5-Bis-trifluoromethyl-phenyl)-N-{2-[(2-methoxy-ethyl)-methyl-amino]-4-oxo-4H-quinazolin-3-yl}-acetamide;
N-[2-(Benzyl-methyl-amino)-4-oxo-4H-quinazolin-3-yl]-2-(3,4-difluoro-phenyl)-acetamide;
2-(3,5-Difluoro-phenyl)-N-(2-morpholin-4-yl-4-oxo-4H-quinazolin-3-yl)-acetamide;
2-(4-Chloro-phenyl)-N-{7-fluoro-2-[(2-methoxy-ethyl)-methyl-amino]-4-oxo-4H-quinazolin-3-yl}-acetamide;
2-(4-Chloro-phenyl)-N-(2-morpholin-4-yl-4-oxo-4H-quinazolin-3-yl)-acetamide;
2-(3,5-Difluoro-phenyl)-N-{7-fluoro-2-[(2-methoxy-ethyl)-methyl-amino]-4-oxo-4H-quinazolin-3-yl}-acetamide;
2-(4-Chloro-phenyl)-N-(2-dimethylamino-4-oxo-4H-quinazolin-3-yl)-acetamide;
N-(2-Diethylamino-6-fluoro-4-oxo-4H-quinazolin-3-yl)-2-(3,5-difluoro-phenyl)-acetamide;
2-(4-Chloro-phenyl)-N-(2-diethylamino-6-fluoro-4-oxo-4H-quinazolin-3-yl)-acetamide;
2-(3,5-Difluoro-phenyl)-N-[2-(4-methyl-piperazin-1-yl)-4-oxo-4H-quinazolin-3-yl]-acetamide;
N-(2-Diethylamino-6-fluoro-4-oxo-4H-quinazolin-3-yl)-2-(3-fluoro-5-trifluoromethyl-phenyl)-acetamide;
N-[2-(Benzyl-methyl-amino)-4-oxo-4H-quinazolin-3-yl]-2-(3,5-difluoro-phenyl)-acetamide;
2-(3,5-Difluoro-phenyl)-N-{2-[(2-methoxy-ethyl)-methyl-amino]-4-oxo-4H-quinazolin-3-yl}-acetamide;
2-(3-Fluoro-5-trifluoromethyl-phenyl)-N-(4-oxo-2-pyrrolidin-1-yl-7-trifluoromethyl-4H-quinazolin-3-yl)-acetamide;
2-(3,5-Difluoro-phenyl)-N-(4-oxo-2-pyrrolidin-1-yl-7-trifluoromethyl-4H-quinazolin-3-yl)-acetamide;
2-(3-Fluoro-5-trifluoromethyl-phenyl)-N-{2-[(2-methoxy-ethyl)-methyl-amino]-4-oxo-7-trifluoromethyl-4H-quinazolin-3-yl}-acetamide;
2-(3,5-Difluoro-phenyl)-N-{2-[(2-methoxy-ethyl)-methyl-amino]-4-oxo-7-trifluoromethyl-4H-quinazolin-3-yl}-acetamide;
N-(6-Butoxy-2-morpholin-4-yl-4-oxo-4H-quinazolin-3-yl)-2-(3,5-difluoro-phenyl)-acetamide;
N-(5-Chloro-4-oxo-2-pyrrolidin-1-yl-4H-quinazolin-3-yl)-2-(3,5-difluoro-phenyl)-acetamide;
N-(5-Chloro-2-diethylamino-4-oxo-4H-quinazolin-3-yl)-2-(3,5-difluoro-phenyl)-acetamide;
N-(2-Diethylamino-7-fluoro-4-oxo-4H-quinazolin-3-yl)-2-(3,5-difluoro-phenyl)-acetamide;
N-(2-Diethylamino-5-fluoro-4-oxo-4H-quinazolin-3-yl)-2-(3,5-difluoro-phenyl)-acetamide;
N-(2-Diethylamino-4-oxo-7-trifluoromethyl-4H-quinazolin-3-yl)-2-(3,5-difluoro-phenyl)-acetamide;
N-(7-Chloro-2-diethylamino-4-oxo-4H-quinazolin-3-yl)-2-(3,5-difluoro-phenyl)-acetamide;
N-(7-Chloro-4-oxo-2-pyrrolidin-1-yl-4H-quinazolin-3-yl)-2-(3,5-difluoro-phenyl)-acetamide;
N-(6-Chloro-2-diethylamino-7-fluoro-4-oxo-4H-quinazolin-3-yl)-2-(3,5-difluoro-phenyl)-acetamide;
N-(2-Diethylamino-5,7-difluoro-4-oxo-4H-quinazolin-3-yl)-2-(3,5-difluoro-phenyl)-acetamide;
2-(3,5-Difluoro-phenyl)-N-(7-fluoro-4-oxo-2-pyrrolidin-1-yl-4H-quinazolin-3-yl)-acetamide;
N-(6-Chloro-7-fluoro-4-oxo-2-pyrrolidin-1-yl-4H-quinazolin-3-yl)-2-(3,5-difluoro-phenyl)-acetamide;
N-(5,7-Difluoro-4-oxo-2-pyrrolidin-1-yl-4H-quinazolin-3-yl)-2-(3,5-difluoro-phenyl)-acetamide;
N-(5,7-Dichloro-2-diethylamino-4-oxo-4H-quinazolin-3-yl)-2-(3,5-difluoro-phenyl)-acetamide;
N-(2-Diethylamino-6,7-difluoro-4-oxo-4H-quinazolin-3-yl)-2-(3,5-difluoro-phenyl)-acetamide;
N-(6,7-Difluoro-4-oxo-2-pyrrolidin-1-yl-4H-quinazolin-3-yl)-2-(3,5-difluoro-phenyl)-acetamide;

2-(3-Fluoro-4-trifluoromethyl-phenyl)-N-(2-morpholin-4-yl-4-oxo-4H-quinazolin-3-yl)-acetamide;
N-(2-Dimethylamino-4-oxo-4H-quinazolin-3-yl)-2-(3-fluoro-4-trifluoromethyl-phenyl)-acetamide;
N-(6-Chloro-2-diethylamino-4-oxo-4H-quinazolin-3-yl)-2-(3,5-difluoro-phenyl)-acetamide;
N-(2-Dimethylamino-6-fluoro-4-oxo-4H-quinazolin-3-yl)-2-(3-fluoro-4-trifluoromethyl-phenyl)-acetamide;
N-(6-Fluoro-4-oxo-2-pyrrolidin-1-yl-4H-quinazolin-3-yl)-2-(3-fluoro-4-trifluoromethyl-phenyl)-acetamide;
2-(4-Chloro-3-fluoro-phenyl)-N-(6-fluoro-4-oxo-2-pyrrolidin-1-yl-4H-quinazolin-3-yl)-acetamide;
2-(3,5-Difluoro-phenyl)-N-(6-fluoro-4-oxo-2-pyrrolidin-1-yl-4H-quinazolin-3-yl)-acetamide;
2-(4-Chloro-3-fluoro-phenyl)-N-(2-dimethylamino-6-fluoro-4-oxo-4H-quinazolin-3-yl)-acetamide;
2-(3,5-Difluoro-phenyl)-N-(2-dimethylamino-6-fluoro-4-oxo-4H-quinazolin-3-yl)-acetamide;
N-(5,7-Dichloro-4-oxo-2-pyrrolidin-1-yl-4H-quinazolin-3-yl)-2-(3,5-difluoro-phenyl)-acetamide;
2-(3,5-Difluoro-phenyl)-N-(2-dimethylamino-5-fluoro-4-oxo-4H-quinazolin-3-yl)-acetamide;
2-(3,5-Difluoro-phenyl)-N-(2-dimethylamino-7-fluoro-4-oxo-4H-quinazolin-3-yl)-acetamide;
N-(2-Dimethylamino-5-fluoro-4-oxo-4H-quinazolin-3-yl)-2-(3-fluoro-5-trifluoromethyl-phenyl)-acetamide;
N-(2-Dimethylamino-7-fluoro-4-oxo-4H-quinazolin-3-yl)-2-(3-fluoro-4-trifluoromethyl-phenyl)-acetamide;
2-(4-Chloro-phenyl)-N-(2-diethylamino-5,7-difluoro-4-oxo-4H-quinazolin-3-yl)-acetamide;
2-(4-Chloro-phenyl)-N-(7-fluoro-4-oxo-2-pyrrolidin-1-yl-4H-quinazolin-3-yl)-acetamide;
2-(3,5-Difluoro-phenyl)-N-[5-fluoro-2-(isopropyl-methyl-amino)-4-oxo-4H-quinazolin-3-yl]-acetamide;
2-(3,5-Difluoro-phenyl)-N-[2-(ethyl-methyl-amino)-5-fluoro-4-oxo-4H-quinazolin-3-yl]-acetamide;
2-(3,5-Difluoro-phenyl)-N-[7-fluoro-2-(isopropyl-methyl-amino)-4-oxo-4H-quinazolin-3-yl]-acetamide;
2-(3,5-Difluoro-phenyl)-N-[2-(ethyl-methyl-amino)-7-fluoro-4-oxo-4H-quinazolin-3-yl]-acetamide;
2-(4-Chloro-phenyl)-N-(7-fluoro-4-oxo-2-pyrrolidin-1-yl-4H-quinazolin-3-yl)-propionamide;
2-(4-Chloro-phenyl)-N-(4-oxo-2-pyrrolidin-1-yl-4H-quinazolin-3-yl)-propionamide;
N-(2-Diethylamino-8-fluoro-4-oxo-4H-quinazolin-3-yl)-2-(3,5-difluoro-phenyl)-acetamide;
2-(3,5-Difluoro-phenyl)-N-(8-fluoro-4-oxo-2-pyrrolidin-1-yl-4H-quinazolin-3-yl)-acetamide;
2-Naphthalen-2-yl-N-(4-oxo-2-pyrrolidin-1-yl-4H-quinazolin-3-yl)-acetamide;
N-(5,7-Difluoro-4-oxo-2-pyrrolidin-1-yl-4H-quinazolin-3-yl)-2-(3,4-difluoro-phenyl)-acetamide;
2-(3,4-Difluoro-phenyl)-N-[2-(ethyl-methyl-amino)-7-fluoro-4-oxo-4H-quinazolin-3-yl]-acetamide;
2-(4-Chloro-phenyl)-N-[2-(ethyl-methyl-amino)-7-fluoro-4-oxo-4H-quinazolin-3-yl]-acetamide;
2-Naphthalen-1-yl-N-(4-oxo-2-pyrrolidin-1-yl-4H-quinazolin-3-yl)-acetamide;
2-(4-Chloro-phenyl)-N-(5,7-difluoro-4-oxo-2-pyrrolidin-1-yl-4H-quinazolin-3-yl)-acetamide;
2-(3,5-Difluoro-phenyl)-N-[2-(ethyl-methyl-amino)-5,7-difluoro-4-oxo-4H-quinazolin-3-yl]-acetamide;
N-[5,7-Difluoro-2-(isopropyl-methyl-amino)-4-oxo-4H-quinazolin-3-yl]-2-(3,4-difluoro-phenyl)-acetamide;
N-[5,7-Difluoro-2-(isopropyl-methyl-amino)-4-oxo-4H-quinazolin-3-yl]-2-(3,5-difluoro-phenyl)-acetamide;
N-[2-(Ethyl-methyl-amino)-7-fluoro-4-oxo-4H-quinazolin-3-yl]-2-(4-methylsulfanyl-phenyl)-acetamide;
2-(4-Isobutyl-phenyl)-N-(4-oxo-2-pyrrolidin-1-yl-4H-quinazolin-3-yl)-propionamide;
N-[2-(Ethyl-methyl-amino)-7-fluoro-4-oxo-4H-quinazolin-3-yl]-2-(4-methoxy-phenyl)-acetamide;
N-(7-Fluoro-4-oxo-2-pyrrolidin-1-yl-4H-quinazolin-3-yl)-2-(4-phenoxy-phenyl)-acetamide;
2-Biphenyl-4-yl-N-(7-fluoro-4-oxo-2-pyrrolidin-1-yl-4H-quinazolin-3-yl)-acetamide;
2-(4-Chloro-phenyl)-N-(4-oxo-2-pyrrolidin-1-yl-4H-quinazolin-3-yl)-acetamide;
2-(3,4-Difluoro-phenyl)-N-(4-oxo-2-pyrrolidin-1-yl-4H-quinazolin-3-yl)-acetamide;
N-[2-(Ethyl-methyl-amino)-7-fluoro-4-oxo-4H-quinazolin-3-yl]-2-(4-isopropyl-phenyl)-acetamide;
2-(3,5-Difluoro-phenyl)-N-[2-(isopropyl-methyl-amino)-4-oxo-4H-1-quinazolin-3-yl]-acetamide;
2-(3,4-Difluoro-phenyl)-N-[2-(isopropyl-methyl-amino)-4-oxo-4,1-quinazolin-3-yl]-acetamide;
2-(3,4-Difluoro-phenyl)-N-(7-fluoro-4-oxo-2-pyrrolidin-1-yl-4H-quinazolin-3-yl)-acetamide;
2-(3,4-Difluoro-phenyl)-N-(8-fluoro-4-oxo-2-pyrrolidin-1-yl-4H-quinazolin-3-yl)-acetamide;
2-(3,4-Difluoro-phenyl)-N-[2-(isobutyl-methyl-amino)-4-oxo-4H-quinazolin-3-yl]-acetamide;
2-(3,5-Difluoro-phenyl)-N-[2-(isobutyl-methyl-amino)-4-oxo-4H-quinazolin-3-yl]-acetamide;
2-(3,4-Difluoro-phenyl)-N-[7-fluoro-2-(isopropyl-methyl-amino)-4-oxo-4H-quinazolin-3-yl]-acetamide;
N-(7-Chloro-6-fluoro-4-oxo-2-pyrrolidin-1-yl-4H-quinazolin-3-yl)-2-(3,5-difluoro-phenyl)-acetamide;
2-(3,5-Difluoro-phenyl)-N-(2-diisopropylamino-4-oxo-4H-quinazolin-3-yl)-acetamide;
N-[2-(Cyclopentyl-methyl-amino)-4-oxo-4H-quinazolin-3-yl]-2-(3,5-difluoro-phenyl)-acetamide;
N-[2-(Cyclopentyl-methyl-amino)-4-oxo-4H-quinazolin-3-yl]-2-(3,4-difluoro-phenyl)-acetamide;
2-(3,4-Difluoro-phenyl)-N-(2-diisopropylamino-4-oxo-4H-quinazolin-3-yl)-acetamide;
2-(3,4-Difluoro-phenyl)-N-(4-oxo-2-piperidin-1-yl-4H-quinazolin-3-yl)-acetamide;
2-(3,5-Difluoro-phenyl)-N-(4-oxo-2-piperidin-1-yl-4H-quinazolin-3-yl)-acetamide;
N-(8-Chloro-4-oxo-2-pyrrolidin-1-yl-4H-quinazolin-3-yl)-2-(3,5-difluoro-phenyl)-acetamide;
N-(2-Diethylamino-6-hydroxy-4-oxo-4H-quinazolin-3-yl)-2-(3,5-difluoro-phenyl)-acetamide;
N-(6,8-Dichloro-2-diethylamino-4-oxo-4H-quinazolin-3-yl)-2-(3,5-difluoro-phenyl)-acetamide;
N-(6-Amino-2-diethylamino-4-oxo-4H-quinazolin-3-yl)-2-(3,5-difluoro-phenyl)-acetamide;
N-(7-Amino-2-diethylamino-4-oxo-4H-quinazolin-3-yl)-2-(3,5-difluoro-phenyl)-acetamide;
N-(7-Amino-4-oxo-2-pyrrolidin-1-yl-4H-quinazolin-3-yl)-2-(3,5-difluoro-phenyl)-acetamide; or
a pharmaceutically-acceptable addition salt thereof.

Any combination of two or more of the embodiments described herein is considered within the scope of the present invention.

Definition of Substituents

In the context of this invention an alkyl group designates a univalent saturated, straight or branched hydrocarbon chain containing from one to eighteen carbon atoms ($C_{1-18}$-alkyl), e.g. from one to six carbon atoms ($C_{1-6}$-alkyl; lower alkyl), including pentyl, isopentyl, neopentyl, hexyl and isohexyl. In one embodiment alkyl represents a $C_{1-4}$-alkyl group, including butyl, isobutyl, secondary butyl, and tertiary butyl. In another embodiment of this invention alkyl represents a $C_{1-3}$-alkyl group, which may be methyl, ethyl, propyl or isopropyl.

In the context of this invention a cycloalkyl group designates a cyclic alkyl group, containing from three to seven carbon atoms ($C_{3-7}$-cycloalkyl), including cyclopropyl, cyclobutyl, cyclopentyl, cyclohexyl and cycloheptyl.

In the context of this invention halo represents fluoro, chloro, bromo or iodo. Thus a trihalomethyl group represents e.g. a trifluoromethyl group, a trichloromethyl group, and similar trihalo-substituted methyl groups.

In the context of this invention a haloalkyl group designates an alkyl group as defined herein, which alkyl group is substituted one or more times with halo. Examples of haloalkyl groups of the invention include trihalomethyl, e.g. trifluoromethyl.

In the context of this invention a hydroxy-alkyl group designates an alkyl group as defined above, which alkyl group is substituted with one or more hydroxy groups. Examples of hydroxy-alkyl groups of the invention include 2-hydroxy-methyl, 2-hydroxy-ethyl, 3-hydroxy-propyl, 4-hydroxy-butyl, 5-hydroxy-pentyl and 6-hydroxy-hexyl.

In the context of this invention a phenyl-alkyl group designates an alkyl group as defined above, which alkyl group is substituted with a phenyl group. Examples of phenyl-alkyl groups of the invention include phenyl-propyl, phenyl-ethyl and benzyl.

In the context of this invention an alkoxy group designates an "alkyl-O—" group, wherein alkyl is as defined above. Examples of alkoxy groups of the invention include methoxy, ethoxy and propoxy.

In the context of this invention an "alkyl-sulfanyl" group designates an "alkyl-S—" group, wherein alkyl is as defined above. Examples of alkyl-sulfanyl groups of the invention include methylthio, ethylthio and propylthio.

In the context of this invention an "alkyl-sulfonyl" group designates an "alkyl-$SO_2$—" group, wherein alkyl is as defined above. Examples of alkyl-sulfonyl groups of the invention include methylsulfonyl, ethylsulfonyl, propylsulfonyl, butylsulfonyl, pentylsulfonyl and hexylsulfonyl.

In the context of this invention an alkyl-carbonyl-amino group designates an "alkyl-CO—NH—" group, wherein alkyl is as defined above. Examples of alkyl-carbonyl-amino groups of the invention include acetamido.

Pharmaceutically Acceptable Salts

The 2,3-diamino-quinazolinone derivatives of the invention may be provided in any form suitable for the intended administration. Suitable forms include pharmaceutically (i.e. physiologically) acceptable salts, and pre- or prodrug forms of the 2,3-diamino-quinazolinone derivatives of the invention.

Examples of pharmaceutically acceptable addition salts include, without limitation, the non-toxic inorganic and organic acid addition salts such as the hydro-chloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulphonate derived from benzensulphonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulphonate derived from methane sulphonic acid, the naphthalene-2-sulphonate derived from naphtalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Examples of pharmaceutically acceptable cationic salts of a chemical compound of the invention include, without limitation, the sodium, the potassium, the calcium, the magnesium, the zinc, the aluminium, the lithium, the choline, the lysine, and the ammonium salt, and the like, of a chemical compound of the invention containing an anionic group. Such cationic salts may be formed by procedures well known and described in the art.

Examples of pharmaceutically acceptable addition salts include, without limitation, the non-toxic inorganic and organic acid addition salts such as the hydro-chloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate derived, the phthalate, the salicylate, the sorbate, the stearate, the succinate, the tartrate, the toluene-p-sulphonate, and the like. Such salts may be formed by procedures well known and described in the art.

Examples of pharmaceutically acceptable cationic salts of a chemical compound of the invention include, without limitation, the sodium, the potassium, the calcium, the magnesium, the zinc, the aluminium, the lithium, the choline, the lysine, and the ammonium salt, and the like, of a chemical compound of the invention containing an anionic group. Such cationic salts may be formed by procedures well known and described in the art.

Steric Isomers

The 2,3-diamino-quinazolinone derivatives of the present invention may exist in (+) and (−) forms as well as in racemic forms (±). The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l- (tartrates, mandelates, or camphorsulphonate) salts for example.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Optical active compounds can also be prepared from optical active starting materials.

Methods of Preparation

The 2,3-diamino-quinazolinone derivatives of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

The 2,3-diamino-quinazolinone derivatives of the invention have been found useful as modulators of the $K_v7$ (KCNQ) potassium channels. At present five such channels are known, i.e. the $K_v7.1$ (KCNQ1) channel, the $K_v7.2$ (KCNQ2) channel, the $K_v7.3$ (KCNQ3) channel, the $K_v7.4$ (KCNQ4) channel, and the $K_v7.5$ (KCNQ5) channel, and heteromeric combinations hereof. Moreover, the modulatory activity may be inhibitory (i.e. inhibitory activity) or stimulatory (i.e. activating activity).

The modulatory activity may be determined using conventional methods, e.g. binding or activity studies, known in the art, or as described in the working examples.

In one embodiment the 2,3-diamino-quinazolinone derivatives of the invention show stimulating activity at $K_v7.2$, $K_v7.3$, $K_v7.4$ and/or $K_v7.5$ potassium channels, and heteromeric combinations hereof. Compounds of the invention are selective, e.g. showing $K_v7.2$ potassium channel activation.

Accordingly, the compounds of the invention are considered useful for treatment, prevention or alleviation of a disease or a disorder or a condition of a living animal body, including a human, which disorder, disease or condition is responsive to modulation of a $K_v7$ potassium channel.

Due to the distribution of $K_v7$ channels within the organism, $K_v7$ channel modulators are considered useful for the treatment or alleviation of conditions as diverse as pain, migraine, tension type headache, PNS disorders, CNS disorders, CNS damage caused by trauma, stroke or neurodegenerative illness or diseases, learning and cognitive disorders, motion and motor disorders, multiple sclerosis, heart failure, cardiomyopathia, cardiac disorders, inflammatory diseases, ophthalmic conditions, progressive hearing loss or tinnitus, obstructive or inflammatory airway diseases, for inducing or maintaining bladder control including the treatment or prevention of urinary incontinence, nocturia, bladder spasms, overactive bladder (OAB), bladder outflow obstruction, painful bladder syndrome and interstitial cystitis (IC).

In one embodiment the compounds of the invention are considered useful for treatment, prevention or alleviation of a disease, disorder or adverse condition of the CNS. In a more specific embodiment, the disease, disorder or condition is an affective disorder, a neuro-physiological disorder, anxiety, depression, a bipolar disorder, mania, a sleep disorder, addiction, an eating disorder, a phobia, Parkinson's disease, a mood disorder, a psychotic disorder, a compulsive behaviour, mania, psychosis or schizophrenia.

In another embodiment the disease, disorder or condition contemplated according to the invention is schizophrenia.

In another embodiment the disease, disorder or condition contemplated according to the invention is anxiety.

In another embodiment the compounds of the invention are considered useful for treatment, prevention or alleviation of a CNS damage caused by trauma or by a spinal cord damage, stroke, a neurodegenerative illness or disease, dementia, Alzheimer's disease, a motor neuron disease, a Parkinson-like motor disorder, multiple sclerosis, amyelotrophic lateral sclerosis (ALS), HIV dementia, Huntington's disease, Pick's disease, torsades de pointes, tremor, muscle spasms, myasthenia gravis, convulsions, ataxia, myokymia, seizures, epilepsy or spasticity.

In another embodiment the disease, disorder or condition contemplated according to the invention is epilepsy.

In another embodiment the compounds of the invention are considered useful for treatment, prevention or alleviation of pain, including acute and chronic pain, neuropathic pain, central pain, or pain related to diabetic neuropathy, to postherpetic neuralgia, to peripheral nerve injury or drug addiction, migraine and migraine-related disorders and to tension-type headache. In a more specific embodiment the pain is somatic pain, incl. visceral pain or cutaneous pain, or pain caused by inflammation or by infection. In another specific embodiment the pain is neuropathic, e.g. caused by injury to the central or peripheral nervous system, e.g. due to tissue trauma, infection, diabetes, an autoimmune disease, arthritis or neuralgia.

In another embodiment the compounds of the invention are considered useful for treatment, prevention or alleviation of a learning and cognitive disorder, memory dysfunction, memory impairment or age-associated memory loss.

In another embodiment the compounds of the invention are considered useful for treatment, prevention or alleviation of a disease, disorder or condition associated with the heart or skeletal muscle, heart failure, cardiomyopathia, cardiac arrhythmia, cardiac ischaemia or long QT syndrome.

In another embodiment the compounds of the invention are considered useful for treatment, prevention or alleviation of an inflammatory disease or condition, inflammatory bowel disease, Crohn's disease, ulcerative colitis or Creutzfeld-Jacobs disease.

In another embodiment the compounds of the invention are considered useful for treatment, prevention or alleviation of asthma, an obstructive or inflammatory airway disease, an airway hyper reactivity, a pneumoconiosis such as aluminosis, anthracosis, asbestosis, chalicosis, ptilosis, siderosis, silicosis, tabacosis and byssinosis, a chronic obstructive pulmonary disease (COPD), excerbation of airways hyper reactivity or cystic fibrosis.

In another embodiment the compounds of the invention are considered useful for treatment, prevention or alleviation of progressive hearing loss or tinnitus, an ophthalmic disorder, a drug-dependence or drug-addiction disorder, hyperactive gastric motility or urinary incontinence.

In another embodiment the compounds of the invention are considered useful for inducing or maintaining bladder control including the treatment or prevention of urinary incontinence, nocturia, bladder spasms, overactive bladder (OAB), bladder outflow obstruction and interstitial cystitis (IC).

In another embodiment the compounds of the invention are considered useful for treatment, prevention or alleviation of pain, neurodegenerative disorders, migraine, bipolar disorders, mania, epilepsy, convulsions, seizures and seizure disorders, anxiety, depression, functional bowel disorders and multiple sclerosis.

In another embodiment the compounds of the invention are considered useful for treatment, prevention or alleviation of pain, including mild, moderate or even severe pain of acute, chronic or recurrent character, as well as neuropathic pain and pain caused by migraine, postoperative pain, phantom limb pain, neuronal hyperexcitability disorders, peripheral nerve hyperexcitability, neuropathic pain, chronic headache, tension type headache, central pain, pain related to diabetic neuropathy, to post therapeutic neuralgia, or to peripheral nerve injury.

In another embodiment the compounds of the invention are considered useful for treatment, prevention or alleviation of pain or neuropathic pain.

In another embodiment the compounds of the invention are considered useful for treatment, prevention or alleviation of epilepsy or anxiety.

Pharmaceutical Compositions

Viewed from one aspect the invention relates to the use of a 2,3-diamino-quinazolinone derivative of the invention, or a pharmaceutically-acceptable addition salt thereof, for the manufacture of a pharmaceutical composition for the treatment, prevention or alleviation of a disease or a disorder or a condition of a mammal, including a human, which disease, disorder or condition is responsive to modulation of $K_v7$ channels.

Viewed from another aspect, the invention provides pharmaceutical compositions comprising a therapeutically-effective amount of a 2,3-diamino-quinazolinone derivative of the invention, or a pharmaceutically-acceptable addition salt thereof, together with at least one pharmaceutically-acceptable carrier or diluent, for the treatment, prevention or alleviation of a disease or a disorder or a condition that is responsive to modulation of $K_v7$ channels.

While a 2,3-diamino-quinazolinone derivative for use according to the invention may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In another embodiment, the invention provides pharmaceutical compositions comprising a 2,3-diamino-quinazolinone derivative of the invention, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route which suite the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition may be prepared by the skilled person using standard and conventional techniques appropriate for the desired formulation. When desired, compositions adapted to give sustained release of the active ingredient may be employed.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The chemical compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, supposetories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion)

and may be presented in unit dose form in ampoules, prefilled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations, intended for conversion shortly before use to liquid form preparations for oral administration. Such liquid forms include solutions, suspensions, and emulsions. In addition to the active component such preparations may comprise colorants, flavours, stabilisers, buffers, artificial and natural sweeteners, dispersants, thickeners, solubilizing agents, and the like.

For topical administration to the epidermis the chemical compound of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavored base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form.

Administration to the respiratory tract may also be achieved by means of an aerosol formulation in which the active ingredient is provided in a pressurized pack with a suitable propellant such as a chlorofluorocarbon (CFC) for example dichloro-difluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of *Remington's Pharmaceutical Sciences* (Maack Publishing Co., Easton, Pa.).

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Methods of Therapy

In another aspect the invention provides a method for the treatment, prevention or alleviation of a disease or a disorder or a condition of a living animal body, including a human, which disease, disorder or condition is responsive to activation of $K_v7$ channels, and which method comprises administering to such a living animal body, including a human, in need thereof an effective amount of a 2,3-diamino-quinazolinone derivative of the invention.

The preferred medical indications contemplated according to the invention are those stated above.

It is at present contemplated that suitable dosage ranges are 0.1 to 2000 milligrams daily, 10-1000 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

A satisfactory result can, in certain instances, be obtained at a dosage as low as 0.005 mg/kg i.v. and 0.01 mg/kg p.o. The upper limit of the dosage range is about 30 mg/kg i.v. and 500 mg/kg p.o. Preferred ranges are from about 0.001 to about 100 mg/kg i.v. and from about 0.1 to about 30 mg/kg p.o.

EXAMPLES

The invention is further illustrated with reference to the following examples, which are not intended to be in any way limiting to the scope of the invention as claimed.

Example 1

Preparative Example

The compounds of the invention may be synthesized as outlined in general terms and described in more details below.

Method A0

Methyl 2-amino-4-fluorobenzoate (Intermediate Compound)

2-Amino-4-fluorobenzoic acid (10.0 g, 64.5 mmol) was dissolved in methanol (50 mL) and toluene (150 mL). (Trimethylsilyl)diazomethane (2M in diethyl ether, 48.3 mL, 96.7 mmol) was added over 10 minutes at RT. Stirring was continued for 2 h at RT. Water (300 mL) was added to the mixture and the volatiles were removed in vacuo. The remaining aqueous phase was cooled to 0° C. for 30 minutes and the

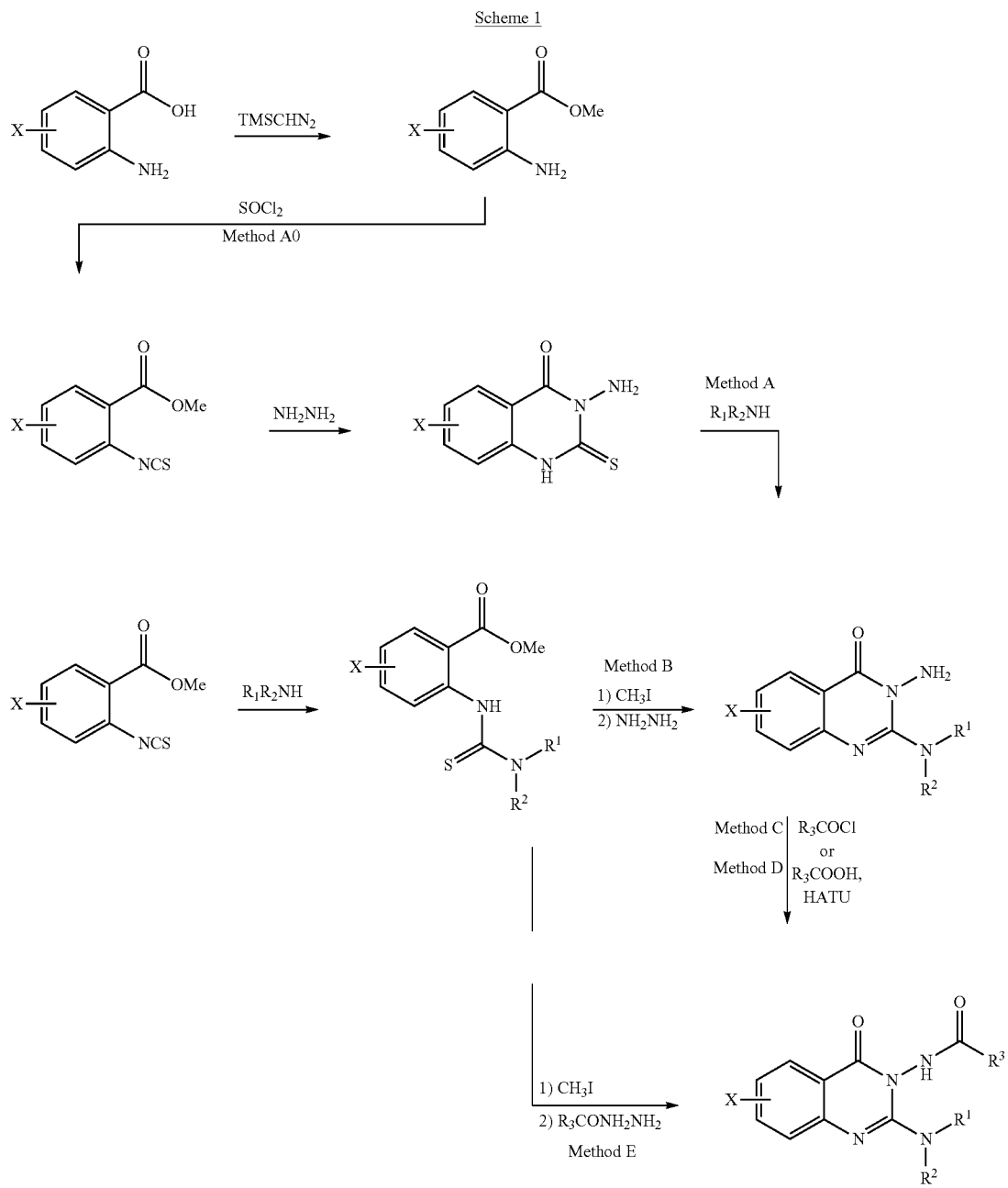

formed precipitate was collected by filtration, washed with water and dried to give pure title compound (10.4 g, 95%).

Methyl 4-fluoro-2-isothiocyanatobenzoate

Methyl 2-amino-4-fluorobenzoate (7.3 g, 43.2 mmol) was dissolved in chloro-form, followed by addition of water (150 mL) and sodium hydrogencarbonate (36.3 g, 432 mmol). Thiophosgene (3.73 mL, 47.5 mmol) was added and the mixture was stirred at RT for 2 h. Water (250 mL) was added and the mixture was extracted with DCM. The combined organics were dried ($MgSO_4$) and evaporated to give the title compound (8.90 g, 98%).

Method A

3-Amino-2-thioxo-2,3-dihydro-1H-quinazolin-4-one (Intermediate Compound)

Methyl 2-isothiocyanatobenzoate (5.00 g, 25.9 mmol) was dissolved in THF (125 mL), followed by addition of hydrazine monohydrate (2.51 mL, 51.8 mmol). The reaction mixture was refluxed for 1 h, cooled to RT and the precipitate was collected by filtration. The precipitate was washed with water and dried in vacuo to give pure title compound (4.78 g, 96%).

3-Amino-2-pyrrolidin-1-yl-3H-quinazolin-4-one (Intermediate Compound)

3-Amino-2-thioxo-2,3-dihydro-1H-quinazolin-4-one (0.200 g, 1.04 mmol) was dissolved in pyrrolidine (0.850 mL, 10.4 mmol) and the mixture was heated at 150° C. for 20 minutes under microwave conditions. After cooling the mixture was diluted with water and extracted with EtOAc. The combined organics were washed with water and brine, dried ($Na_2SO_4$) and evaporated in vacuo to give the title compound (0.180 g, 75%).

Method B

Methyl 2-(3,3-diethyl-thioureido)benzoate (Intermediate Compound)

Methyl 2-isothiocyanatobenzoate (3.37 g, 17.4 mmol) was dissolved in THF (75 mL), followed by addition of diethylamine (3.59 mL, 34.9 mmol). The reaction mixture was stirred at RT. After 1 h the mixture was poured into water (400 mL). The formed precipitate was collected by filtration, washed with water and dried in vacuo to give pure title compound (4.24 g, 91%).

3-Amino-2-diethylamino-3H-quinazolin-4-one (Intermediate Compound)

Methyl 2-(3,3-diethyl-thioureido)benzoate (2.29 g, 8.59 mmol) was dissolved in methanol (15 mL), followed by addition of iodomethane (1.07 mL, 17.2 mmol). The reaction mixture was heated at 80° C. for 10 minutes under microwave conditions making sure the temperature did not exceed 80° C. The reaction mixture was evaporated to dryness and then redissolved in methanol (50 mL). Hydrazine monohydrate (1.25 mL, 25.8 mmol) was added followed by stirring at RT overnight. The reaction mixture was poured into water (200 mL), followed by extraction with diethyl ether (2×100 mL), drying ($MgSO_4$) and evaporation in vacuo. The crude product was subjected to column chromatography (EtOAc/Heptane) giving the title compound (1.37 g, 69%).

Method C 2-(3,5-Difluoro-phenyl)-N-(4-oxo-2-pyrrolidin-1-yl-4H-quinazolin-3-yl)-acetamide (Compound C1)

3,5-Difluorophenylacetic acid (0.227 g, 1.30 mmol) was dissolved in DCM (5 mL), followed by addition of oxalyl chloride (137 µL, 1.56 mmol) and 2 drops of dry DMF. After 1 hour gas evolution had stopped and pyridine (106 µL, 1.30 mmol) was added, followed by addition of 3-amino-2-pyrrolidin-1-yl-3H-quinazolin-4-one. After stirring at RT for 5 minutes additional pyridine (212 µL, 2.60 mmol) was added. The reaction mixture was stirred overnight at RT. The mixture was diluted with EtOAc (20 mL), washed with 1 M HCl (20 mL), dried ($MgSO_4$) and evaporated in vacuo. The crude product was subjected to column chromatography (EtOAc/Heptane) giving the title compound (0.073 g, 15%). LC-ESI-HRMS of $[M+H]^+$ shows 385,1485 Da. Calc. 385,147607 Da.

Method D 2-(3,5-Difluoro-phenyl)-N-(4-oxo-2-thiazolidin-3-yl-4H-quinazolin-3-yl)-acetamide (Compound D1)

3,5-Difluorophenylacetic acid (0.152 g, 0.88 mmol), 3-Amino-2-thiazolidin-3-yl-3H-quinazolin-4-one (0.146 g, 0.59 mmol) and HATU (0.268 g, 0.71 mmol) were dissolved in dry DMF (2.5 mL), followed by addition of 2,6-lutidine (205 µL, 1.76 mmol). The reaction mixture was stirred at RT for 48 h and then poured into 1 M HCl (20 mL). The formed precipitate was collected by filtration and washed with water and heptane, which after drying gave the title compound (0.180 g, 76%). LC-ESI-HRMS of $[M+H]^+$ shows 403,1047 Da. Calc. 403,104028 Da.

Method E

N-(2-Diethylamino-4-oxo-4H-quinazolin-3-yl)-2-phenyl-acetamide (Compound E1)

Methyl 2-(3,3-diethyl-thioureido)benzoate (0.500 g, 1.88 mmol) was dissolved in methanol (10 mL), followed by addition of iodomethane (234 µL, 3.75 mmol). The reaction mixture was heated at 80° C. for 10 minutes under microwave conditions making sure the temperature did not exceed 80° C. The reaction mixture was evaporated to dryness and then redissolved in ethanol (20 mL), followed by addition of phenylacetic acid hydrazide (0.367 g, 2.44 mmol). The mixture was stirred for 48 h at reflux. After cooling the mixture was filtered and the filtrate was evaporated to dryness. The crude product was purified by column chromatography (EtOAc/Heptane) giving the title compound (0.089 g, 14%). LC-ESI-HRMS of $[M+H]^+$ shows 351,1818 Da. Calc. 351,182101 Da.

Using Method A0+B+C the following compounds were synthesized 2-(3,5-Difluoro-phenyl)-N-(2-dimethylamino-4-oxo-4H-quinazolin-3-yl)-acetamide (Compound C2)

LC-ESI-HRMS of $[M+H]^+$ shows 359,1309 Da. Calc. 359,131957 Da.

2-(4-Chloro-phenyl)-N-(2-diethylamino-4-oxo-4H-quinazolin-3-yl)-acetamide (Compound C3)

LC-ESI-HRMS of [M+H]+ shows 385,1417 Da. Calc. 385,143129 Da.

2-(3,5-Difluoro-phenyl)-N-[2-(ethyl-methyl-amino)-4-oxo-4H-quinazolin-3-yl]-acetamide (Compound C4)

LC-ESI-HRMS of [M+H]+ shows 373,1464 Da. Calc. 373,147607 Da.

2-(3,5-Difluoro-phenyl)-N-(2-dimethylamino-4-oxo-7-trifluoromethyl-4H-quinazolin-3yl)-propionamide (Compound C5)

LC-ESI-HRMS of [M+H]+ shows 441.1348 Da. Calc. 441.134991 Da.

N-(2-Diethylamino-4-oxo-4H-quinazolin-3-yl)-2-(4-methanesulfonyl-phenyl)-acetamide (Compound C6)

LC-ESI-HRMS of [M+H]+ shows 429.1585 Da. Calc. 429.159652 Da

N-{2-[(2-Methoxy-ethyl)-methyl-amino]-4-oxo-4H-quinazolin-3-yl}-2-(4-trifluoromethyl-phenyl)-acetamide (Compound C7)

LC-ESI-HRMS of [M+H]+ shows 435.1648 Da. Calc. 435.1644 Da 2-(4-Butoxy-phenyl)-N-{2-[(2-methoxy-ethyl)-methyl-amino]-4-oxo-4H-quinazolin-3-yl}-acetamide (Compound C8)

LC-ESI-HRMS of [M+H]+ shows 439.2343 Da. Calc. 439.234531 Da

N-[2-(Benzyl-methyl-amino)-4-oxo-4H-quinazolin-3-yl]-2-(4-methanesulfonyl-phenyl)-acetamide (Compound C9)

LC-ESI-HRMS of [M+H]+ shows 477.1581 Da. Calc. 477.159652 Da 2-(4-Butoxy-phenyl)-N-(4-oxo-2-pyrrolidin-1-yl-4H-quinazolin-3-yl)-acetamide (Compound C10)

LC-ESI-HRMS of [M+H]+ shows 421.2227 Da. Calc. 421.223966 Da 2-(3-Fluoro-4-trifluoromethyl-phenyl)-N-(4-oxo-2-pyrrolidin-1-yl-4H-quinazolin-3-yl)-acetamide (Compound C11)

LC-ESI-HRMS of [M+H]+shows 435.1424 Da. Calc. 435.144413 Da.

2-(3,5-Bis-trifluoromethyl-phenyl)-N-{2-[(2-methoxy-ethyl)-methyl-amino]-4-oxo-4H-quinazolin-3-yl}-acetamide (Compound C12)

LC-ESI-HRMS of [M+H]+shows 503.1496 Da. Calc. 503.151784 Da.

N-[2-(Benzyl-methyl-amino)-4-oxo-4H-quinazolin-3-yl]-2-(3,4-difluoro-phenyl)-acetamide (Compound C13)

LC-ESI-HRMS of [M+H]+ shows 435.1613 Da. Calc. 435.163257 Da.

2-(3,5-Difluoro-phenyl)-N-(2-morpholin-4-yl-4-oxo-4H-quinazolin-3-yl)-acetamide (Compound C14)

LC-ESI-HRMS of [M+H]+ shows 401.1405 Da. Calc. 401.142522 Da.

2-(4-Chloro-phenyl)-N-{7-fluoro-2-[(2-methoxy-ethyl)-methyl-amino]-4-oxo-4H-quinazolin-3-yl}-acetamide (Compound C15)

LC-ESI-HRMS of [M+H]+ shows 419.1284 Da. Calc. 419.128622 Da.

2-(4-Chloro-phenyl)-N-(2-morpholin-4-yl-4-oxo-4H-quinazolin-3-yl)-acetamide (Compound C16)

LC-ESI-HRMS of [M+H]+ shows 399.1206 Da. Calc. 399.122394 Da.

2-(3,5-Difluoro-phenyl)-N-{7-fluoro-2-[(2-methoxy-ethyl)-methyl-amino]-4-oxo-4H-quinazolin-3-yl}-acetamide (Compound C17)

LC-ESI-HRMS of [M+H]+ shows 421.1481 Da. Calc. 421.14875 Da.

2-(4-Chloro-phenyl)-N-(2-dimethylamino-4-oxo-4H-quinazolin-3-yl)-acetamide (Compound C18)

LC-ESI-HRMS of [M+H]+ shows 357.1113 Da. Calc. 357.111829 Da.

N-(2-Diethylamino-6-fluoro-4-oxo-4H-quinazolin-3-yl)-2-(3,5-difluoro-phenyl)-acetamide (Compound C19)

LC-ESI-HRMS of [M+H]+ shows 405.1551 Da. Calc. 405.153835 Da.

2-(4-Chloro-phenyl)-N-(2-diethylamino-6-fluoro-4-oxo-4H-quinazolin-3-yl)-acetamide (Compound C20)

LC-ESI-HRMS of [M+H]+ shows 403.1342 Da. Calc. 403.133707 Da.

2-(3,5-Difluoro-phenyl)-N-[2-(4-methyl-piperazin-1-yl)-4-oxo-4H-quinazolin-3-yl]-acetamide (Compound C21)

LC-ESI-HRMS of [M+H]+ shows 414.1724 Da. Calc. 414.174156 Da.

N-(2-Diethylamino-6-fluoro-4-oxo-4H-quinazolin-3-yl)-2-(3-fluoro-5-trifluoromethyl-phenyl)-acetamide (Compound C22)

LC-ESI-HRMS of [M+H]+ shows 455.1506 Da. Calc. 455.150641 Da.

N-[2-(Benzyl-methyl-amino)-4-oxo-4H-quinazolin-3-yl]-2-(3,5-difluoro-phenyl)-acetamide (Compound C23)

LC-ESI-HRMS of [M+H]$^+$ shows 435.1654 Da. Calc. 435.163257 Da.

2-(3,5-Difluoro-phenyl)-N-{2-[(2-methoxy-ethyl)-methyl-amino]-4-oxo-4H-quinazolin-3-yl}-acetamide (Compound C24)

LC-ESI-HRMS of [M+H]$^+$ shows 403.1572 Da. Calc. 403.158172 Da.

2-(3-Fluoro-5-trifluoromethyl-phenyl)-N-(4-oxo-2-pyrrolidin-1-yl-7-trifluoromethyl-4H-quinazolin-3-yl)-acetamide (Compound C25)

LC-ESI-HRMS of [M+H]$^+$ shows 503.1316 Da. Calc. 503.131797 Da.

2-(3,5-Difluoro-phenyl)-N-(4-oxo-2-pyrrolidin-1-yl-7-trifluoromethyl-4H-quinazolin-3-yl)-acetamide (Compound C26)

LC-ESI-HRMS of [M+H]$^+$ shows 453.136 Da. Calc. 453.134991 Da.

2-(3-Fluoro-5-trifluoromethyl-phenyl)-N-{2-[(2-methoxy-ethyl)-methyl-amino]-4-oxo-7-trifluoromethyl-4H-quinazolin-3-yl}-acetamide (Compound C27)

LC-ESI-HRMS of [M+H]$^+$ shows 521.1437 Da. Calc. 521.142362 Da.

2-(3,5-Difluoro-phenyl)-N-{2-[(2-methoxy-ethyl)-methyl-amino]-4-oxo-7-trifluoromethyl-4H-quinazolin-3-yl}-acetamide (Compound C28)

LC-ESI-HRMS of [M+H]$^+$ shows 471.1457 Da. Calc. 471.145556 Da.

N-(6-Butoxy-2-morpholin-4-yl-4-oxo-4H-quinazolin-3-yl)-2-(3,5-difluoro-phenyl)-acetamide (Compound C29)

LC-ESI-HRMS of [M+H]$^+$ shows 473.199 Da. Calc. 473.200037 Da.

N-(5-Chloro-4-oxo-2-pyrrolidin-1-yl-4H-quinazolin-3-yl)-2-(3,5-difluoro-phenyl)-acetamide (Compound C30)

LC-ESI-HRMS of [M+H]$^+$ shows 419.1084 Da. Calc. 419.108635 Da.

N-(5-Chloro-2-diethylamino-4-oxo-4H-quinazolin-3-yl)-2-(3,5-difluoro-phenyl)-acetamide (Compound C31)

LC-ESI-HRMS of [M+H]$^+$ shows 421.1234 Da. Calc. 421.124285 Da.

N-(2-Diethylamino-7-fluoro-4-oxo-4H-quinazolin-3-yl)-2-(3,5-difluoro-phenyl)-acetamide (Compound C32)

LC-ESI-HRMS of [M+H]$^+$ shows 405.1524 Da. Calc. 405.153835 Da.

N-(2-Diethylamino-5-fluoro-4-oxo-4H-quinazolin-3-yl)-2-(3,5-difluoro-phenyl)-acetamide (Compound C33)

LC-ESI-HRMS of [M+H]$^+$ shows 405.1523 Da. Calc. 405.153835 Da.

N-(2-Diethylamino-4-oxo-7-trifluoromethyl-4H-quinazolin-3-yl)-2-(3,5-difluoro-phenyl)-acetamide (Compound C34)

LC-ESI-HRMS of [M+H]$^+$ shows 455.1504 Da. Calc. 455.150641 Da.

N-(7-Chloro-2-diethylamino-4-oxo-4H-quinazolin-3-yl)-2-(3,5-difluoro-phenyl)-acetamide (Compound C35)

LC-ESI-HRMS of [M+H]$^+$ shows 421.1261 Da. Calc. 421.124285 Da.

N-(7-Chloro-4-oxo-2-pyrrolidin-1-yl-4H-quinazolin-3-yl)-2-(3,5-difluoro-phenyl)-acetamide (Compound C36)

LC-ESI-HRMS of [M+H]$^+$ shows 419.1102 Da. Calc. 419.108635 Da.

N-(6-Chloro-2-diethylamino-7-fluoro-4-oxo-4H-quinazolin-3-yl)-2-(3,5-difluoro-phenyl)-acetamide (Compound C37)

LC-ESI-HRMS of [M+H]$^+$ shows 439.1154 Da. Calc. 439.114863 Da.

N-(2-Diethylamino-5,7-difluoro-4-oxo-4H-quinazolin-3-yl)-2-(3,5-difluoro-phenyl)-acetamide (Compound C38)

LC-ESI-HRMS of [M+H]$^+$ shows 423.1428 Da. Calc. 423.144413 Da.

2-(3,5-Difluoro-phenyl)-N-(7-fluoro-4-oxo-2-pyrrolidin-1-yl-4H-quinazolin-3-yl)-acetamide (Compound C39)

LC-ESI-HRMS of [M+H]$^+$ shows 403.14 Da. Calc. 403.138185 Da.

N-(6-Chloro-7-fluoro-4-oxo-2-pyrrolidin-1-yl-4H-quinazolin-3-yl)-2-(3,5-difluoro-phenyl)-acetamide (Compound C40)

LC-ESI-HRMS of [M+H]$^+$ shows 437.099 Da. Calc. 437.099213 Da.

N-(5,7-Difluoro-4-oxo-2-pyrrolidin-1-yl-4H-quinazolin-3-yl)-2-(3,5-difluoro-phenyl)-acetamide (Compound C41)

LC-ESI-HRMS of [M+H]$^+$ shows 421.1297 Da. Calc. 421.128763 Da.

N-(5,7-Dichloro-2-diethylamino-4-oxo-4H-quinazolin-3-yl)-2-(3,5-difluoro-phenyl)-acetamide (Compound C42)

LC-ESI-HRMS of [M+H]$^+$ shows 455.0861 Da. Calc. 455.085313 Da.

N-(2-Diethylamino-6,7-difluoro-4-oxo-4H-quinazolin-3-yl)-2-(3,5-difluoro-phenyl)-acetamide (Compound C43)

LC-ESI-HRMS of [M+H]$^+$ shows 423.1463 Da. Calc. 423.144413 Da.

N-(6,7-Difluoro-4-oxo-2-pyrrolidin-1-yl-4H-quinazolin-3-yl)-2-(3,5-difluoro-phenyl)-acetamide (Compound C44)

LC-ESI-HRMS of [M+H]$^+$ shows 421.1294 Da. Calc. 421.128763 Da.

2-(3-Fluoro-4-trifluoromethyl-phenyl)-N-(2-morpholin-4-yl-4-oxo-4H-quinazolin-3-yl)-acetamide (Compound C45)

LC-ESI-HRMS of [M+H]$^+$ shows 451.1384 Da. Calc. 451.139328 Da.

N-(2-Dimethylamino-4-oxo-4H-quinazolin-3-yl)-2-(3-fluoro-4-trifluoromethyl-phenyl)-acetamide (Compound C46)

LC-ESI-HRMS of [M+H]$^+$ shows 409.1298 Da. Calc. 409.128763 Da.

N-(6-Chloro-2-diethylamino-4-oxo-4H-quinazolin-3-yl)-2-(3,5-difluoro-phenyl)-acetamide (Compound C47)

LC-ESI-HRMS of [M+H]$^+$ shows 421.124 Da. Calc. 421.124285 Da.

N-(2-Dimethylamino-6-fluoro-4-oxo-4H-quinazolin-3-yl)-2-(3-fluoro-4-trifluoromethyl-phenyl)-acetamide (Compound C48)

LC-ESI-HRMS of [M+H]$^+$ shows 427.1199 Da. Calc. 427.119341 Da.

N-(6-Fluoro-4-oxo-2-pyrrolidin-1-yl-4H-quinazolin-3-yl)-2-(3-fluoro-4-trifluoromethyl-phenyl)-acetamide (Compound C49)

LC-ESI-HRMS of [M+H]$^+$ shows 453.1372 Da. Calc. 453.134991 Da.

2-(4-Chloro-3-fluoro-phenyl)-N-(6-fluoro-4-oxo-2-pyrrolidin-1-yl-4H-quinazolin-3-yl)-acetamide (Compound C50)

LC-ESI-HRMS of [M+H]$^+$ shows 419.1093 Da. Calc. 419.108635 Da.

2-(3,5-Difluoro-phenyl)-N-(6-fluoro-4-oxo-2-pyrrolidin-1-yl-4H-quinazolin-3-yl)-acetamide (Compound C51)

LC-ESI-HRMS of [M+H]$^+$ shows 403.1362 Da. Calc. 403.138185 Da.

2-(4-Chloro-3-fluoro-phenyl)-N-(2-dimethylamino-6-fluoro-4-oxo-4H-quinazolin-3-yl)-acetamide (Compound C52)

LC-ESI-HRMS of [M+H]$^+$ shows 393.092 Da. Calc. 393.092985 Da.

2-(3,5-Difluoro-phenyl)-N-(2-dimethylamino-6-fluoro-4-oxo-4H-quinazolin-3-yl)-acetamide (Compound C53)

LC-ESI-HRMS of [M+H]$^+$ shows 377.122 Da. Calc. 377.122535 Da.

N-(5,7-Dichloro-4-oxo-2-pyrrolidin-1-yl-4H-quinazolin-3-yl)-2-(3,5-difluoro-phenyl)-acetamide (Compound C54)

LC-ESI-HRMS of [M+H]$^+$ shows 453.0717 Da. Calc. 453.069663 Da.

2-(3,5-Difluoro-phenyl)-N-(2-dimethylamino-5-fluoro-4-oxo-4H-quinazolin-3-yl)-acetamide (Compound C55)

LC-ESI-HRMS of [M+H]$^+$ shows 377.1205 Da. Calc. 377.122535 Da.

2-(3,5-Difluoro-phenyl)-N-(2-dimethylamino-7-fluoro-4-oxo-4H-quinazolin-3-yl)-acetamide (Compound C56)

LC-ESI-HRMS of [M+H]$^+$ shows 377.1219 Da. Calc. 377.122535 Da.

N-(2-Dimethylamino-5-fluoro-4-oxo-4H-quinazolin-3-yl)-2-(3-fluoro-5-trifluoromethyl-phenyl)-acetamide (Compound C57)

LC-ESI-HRMS of [M+H]$^+$ shows 427.12 Da. Calc. 427.119341 Da.

N-(2-Dimethylamino-7-fluoro-4-oxo-4H-quinazolin-3-yl)-2-(3-fluoro-4-trifluoromethyl-phenyl)-acetamide (Compound C58)

LC-ESI-HRMS of [M+H]$^+$ shows 427.1197 Da. Calc. 427.119341 Da.

2-(4-Chloro-phenyl)-N-(2-diethylamino-5,7-difluoro-4-oxo-4H-quinazolin-3-yl)-acetamide (Compound C59)

LC-ESI-HRMS of [M+H]$^+$ shows 421.1256 Da. Calc. 421.124285 Da.

2-(4-Chloro-phenyl)-N-(7-fluoro-4-oxo-2-pyrrolidin-1-yl-4H-quinazolin-3-yl)-acetamide (Compound C60)

LC-ESI-HRMS of [M+H]$^+$ shows 401.1165 Da. Calc. 401.118057 Da.

2-(3,5-Difluoro-phenyl)-N-[5-fluoro-2-(isopropyl-methyl-amino)-4-oxo-4H-quinazolin-3-yl]-acetamide (Compound C61)

LC-ESI-HRMS of [M+H]$^+$ shows 405.1547 Da. Calc. 405.153835 Da.

2-(3,5-Difluoro-phenyl)-N-[2-(ethyl-methyl-amino)-5-fluoro-4-oxo-4H-quinazolin-3-yl]-acetamide (Compound C62)

LC-ESI-HRMS of [M+H]$^+$ shows 391.1384 Da. Calc. 391.138185 Da.

2-(3,5-Difluoro-phenyl)-N-[7-fluoro-2-(isopropyl-methyl-amino)-4-oxo-4H-quinazolin-3-yl]-acetamide (Compound C63)

LC-ESI-HRMS of [M+H]$^+$ shows 405.1553 Da. Calc. 405.153835 Da.

2-(3,5-Difluoro-phenyl)-N-[2-(ethyl-methyl-amino)-7-fluoro-4-oxo-4H-quinazolin-3-yl]-acetamide (Compound C64)

LC-ESI-HRMS of [M+H]$^+$ shows 391.1369 Da. Calc. 391.138185 Da.

2-(4-Chloro-phenyl)-N-(7-fluoro-4-oxo-2-pyrrolidin-1-yl-4H-quinazolin-3-yl)-propionamide (Compound C65)

LC-ESI-HRMS of [M+H]$^+$ shows 415.135 Da. Calc. 415.133707 Da.

2-(4-Chloro-phenyl)-N-(4-oxo-2-pyrrolidin-1-yl-4H-quinazolin-3-yl)-propionamide (Compound C66)

LC-ESI-HRMS of [M+H]$^+$ shows 397.1435 Da. Calc. 397.143129 Da.

N-(2-Diethylamino-8-fluoro-4-oxo-4H-quinazolin-3-yl)-2-(3,5-difluoro-phenyl)-acetamide (Compound C67)

LC-ESI-HRMS of [M+H]$^+$ shows 405.1538 Da. Calc. 405.153835 Da.

2-(3,5-Difluoro-phenyl)-N-(8-fluoro-4-oxo-2-pyrrolidin-1-yl-4H-quinazolin-3-yl)-acetamide (Compound C68)

LC-ESI-HRMS of [M+H]$^+$ shows 403.1392 Da. Calc. 403.138185 Da.

2-Naphthalen-2-yl-N-(4-oxo-2-pyrrolidin-1-yl-4H-quinazolin-3-yl)-acetamide (Compound C69)

LC-ESI-HRMS of [M+H]$^+$ shows 399.1831 Da. Calc. 399.182101 Da.

N-(5,7-Difluoro-4-oxo-2-pyrrolidin-1-yl-4H-quinazolin-3-yl)-2-(3,4-difluoro-phenyl)-acetamide (Compound C70)

LC-ESI-HRMS of [M+H]$^+$ shows 421.1288 Da. Calc. 421.128763 Da.

2-(3,4-Difluoro-phenyl)-N-[2-(ethyl-methyl-amino)-7-fluoro-4-oxo-4H-quinazolin-3-yl]-acetamide (Compound C71)

LC-ESI-HRMS of [M+H]$^+$ shows 391.1367 Da. Calc. 391.138185 Da.

2-(4-Chloro-phenyl)-N-[2-(ethyl-methyl-amino)-7-fluoro-4-oxo-4H-quinazolin-3-yl]-acetamide (Compound C72)

LC-ESI-HRMS of [M+H]$^+$ shows 389.1166 Da. Calc. 389.118057 Da.

2-Naphthalen-1-yl-N-(4-oxo-2-pyrrolidin-1-yl-4H-quinazolin-3-yl)-acetamide (Compound C73)

LC-ESI-HRMS of [M+H]$^+$ shows 399.1831 Da. Calc. 399.182101 Da.

2-(4-Chloro-phenyl)-N-(5,7-difluoro-4-oxo-2-pyrrolidin-1-yl-4H-quinazolin-3-yl)-acetamide (Compound C74)

LC-ESI-HRMS of [M+H]$^+$ shows 419.1102 Da. Calc. 419.108635 Da.

2-(3,5-Difluoro-phenyl)-N-[2-(ethyl-methyl-amino)-5,7-difluoro-4-oxo-4H-quinazolin-3-yl]-acetamide (Compound C75)

LC-ESI-HRMS of [M+H]$^+$ shows 409.1294 Da. Calc. 409.128763 Da.

N-[5,7-Difluoro-2-(isopropyl-methyl-amino)-4-oxo-4H-quinazolin-3-yl]-2-(3,4-difluoro-phenyl)-acetamide (Compound C76)

LC-ESI-HRMS of [M+H]$^+$ shows 423.1435 Da. Calc. 423.144413 Da.

N-[5,7-Difluoro-2-(isopropyl-methyl-amino)-4-oxo-4H-quinazolin-3-yl]-2-(3,5-difluoro-phenyl)-acetamide (Compound C77)

LC-ESI-HRMS of [M+H]$^+$ shows 423.1431 Da. Calc. 423.144413 Da.

N-[2-(Ethyl-methyl-amino)-7-fluoro-4-oxo-4H-quinazolin-3-yl]-2-(4-methylsulfanyl-phenyl)-acetamide (Compound C78)

LC-ESI-HRMS of [M+H]+ shows 401.1465 Da. Calc. 401.14475 Da.

2-(4-Isobutyl-phenyl)-N-(4-oxo-2-pyrrolidin-1-yl-4H-quinazolin-3-yl)-propionamide (Compound C79)

LC-ESI-HRMS of [M+H]+ shows 419.2463 Da. Calc. 419.244701 Da.

N-[2-(Ethyl-methyl-amino)-7-fluoro-4-oxo-4H-quinazolin-3-yl]-2-(4-methoxy-phenyl)-acetamide (Compound C80)

LC-ESI-HRMS of [M+H]+ shows 385.1666 Da. Calc. 385.167594 Da.

N-(7-Fluoro-4-oxo-2-pyrrolidin-1-yl-4H-quinazolin-3-yl)-2-(4-phenoxy-phenyl)-acetamide (Compound C81)

LC-ESI-HRMS of [M+H]+ shows 459.1833 Da. Calc. 459.183244 Da.

2-Biphenyl-4-yl-N-(7-fluoro-4-oxo-2-pyrrolidin-1-yl-4H-quinazolin-3-yl)-acetamide (Compound C82)

LC-ESI-HRMS of [M+H]+ shows 443.1895 Da. Calc. 443.188329 Da.

2-(4-Chloro-phenyl)-N-(4-oxo-2-pyrrolidin-1-yl-4H-quinazolin-3-yl)-acetamide (Compound C83)

LC-ESI-HRMS of [M+H]+ shows 383.1278 Da. Calc. 383.127479 Da.

2-(3,4-Difluoro-phenyl)-N-(4-oxo-2-pyrrolidin-1-yl-4H-quinazolin-3-yl)-acetamide (Compound C84)

LC-ESI-HRMS of [M+H]+ shows 385.1492 Da. Calc. 385.147607 Da.

N-[2-(Ethyl-methyl-amino)-7-fluoro-4-oxo-4H-quinazolin-3-yl]-2-(4-isopropyl-phenyl)-acetamide (Compound C85)

LC-ESI-HRMS of [M+H]+ shows 397.2037 Da. Calc. 397.203979 Da.

2-(3,5-Difluoro-phenyl)-N-[2-(isopropyl-methyl-amino)-4-oxo-4H-quinazolin-3-yl]-acetamide (Compound C86)

LC-ESI-HRMS of [M+H]+ shows 387.1613 Da. Calc. 387.163257 Da.

2-(3,4-Difluoro-phenyl)-N-[2-(isopropyl-methyl-amino)-4-oxo-4H-quinazolin-3-yl]-acetamide (Compound C87)

LC-ESI-HRMS of [M+H]+ shows 387.1634 Da. Calc. 387.163257 Da.

2-(3,4-Difluoro-phenyl)-N-(7-fluoro-4-oxo-2-pyrrolidin-1-yl-4H-quinazolin-3-yl)-acetamide (Compound C88)

LC-ESI-HRMS of [M+H]+ shows 403.1372 Da. Calc. 403.138185 Da.

2-(3,4-Difluoro-phenyl)-N-(8-fluoro-4-oxo-2-pyrrolidin-1-yl-4H-quinazolin-3-yl)-acetamide (Compound C89)

LC-ESI-HRMS of [M+H]+ shows 403.1376 Da. Calc. 403.138185 Da.

2-(3,4-Difluoro-phenyl)-N-[2-(isobutyl-methyl-amino)-4-oxo-4H-quinazolin-3-yl]-acetamide (Compound C90)

LC-ESI-HRMS of [M+H]+ shows 401.1776 Da. Calc. 401.178907 Da.

2-(3,5-Difluoro-phenyl)-N-[2-(isobutyl-methyl-amino)-4-oxo-4H-quinazolin-3-yl]-acetamide (Compound C91)

LC-ESI-HRMS of [M+H]+ shows 401.1806 Da. Calc. 401.178907 Da.

2-(3,4-Difluoro-phenyl)-N-[7-fluoro-2-(isopropyl-methyl-amino)-4-oxo-4H-quinazolin-3-yl]-acetamide (Compound C92)

LC-ESI-HRMS of [M+H]+ shows 405.1523 Da. Calc. 405.153835 Da.

N-(7-Chloro-6-fluoro-4-oxo-2-pyrrolidin-1-yl-4H-quinazolin-3-yl)-2-(3,5-difluoro-phenyl)-acetamide (Compound C93)

LC-ESI-HRMS of [M+H]+ shows 437.0984 Da. Calc. 437.099213 Da.

2-(3,5-Difluoro-phenyl)-N-(2-diisopropylamino-4-oxo-4H-quinazolin-3-yl)-acetamide (Compound C94)

LC-ESI-HRMS of [M+H]+ shows 415.1933 Da. Calc. 415.194557 Da.

N-[2-(Cyclopentyl-methyl-amino)-4-oxo-4H-quinazolin-3-yl]-2-(3,5-difluoro-phenyl)-acetamide (Compound C95)

LC-ESI-HRMS of [M+H]+ shows 413.1804 Da. Calc. 413.178907 Da.

N-[2-(Cyclopentyl-methyl-amino)-4-oxo-4H-quinazolin-3-yl]-2-(3,4-difluoro-phenyl)-acetamide (Compound C96)

LC-ESI-HRMS of [M+H]+ shows 413.1768 Da. Calc. 413.178907 Da.

2-(3,4-Difluoro-phenyl)-N-(2-diisopropylamino-4-oxo-4H-quinazolin-3-yl)-acetamide (Compound C97)

LC-ESI-HRMS of [M+H]$^+$ shows 415.1924 Da. Calc. 415.194557 Da.

2-(3,4-Difluoro-phenyl)-N-(4-oxo-2-piperidin-1-yl-4H-quinazolin-3-yl)-acetamide (Compound C98)

LC-ESI-HRMS of [M+H]$^+$ shows 399.1615 Da. Calc. 399.163257 Da.

2-(3,5-Difluoro-phenyl)-N-(4-oxo-2-piperidin-1-yl-4H-quinazolin-3-yl)-acetamide (Compound C99)

LC-ESI-HRMS of [M+H]$^+$ shows 399.1646 Da. Calc. 399.163257 Da.

Using Method A0+A+C the following compound was synthesized

N-(8-Chloro-4-oxo-2-pyrrolidin-1-yl-4H-quinazolin-3-yl)-2-(3,5-difluoro-phenyl)-acetamide (Compound C100)

LC-ESI-HRMS of [M+H]$^+$ shows 419.1108 Da. Calc. 419.108635 Da.

Using Method B+D the following compounds were synthesized

N-(2-Diethylamino-4-oxo-4H-quinazolin-3-yl)-2-(3,5-difluoro-phenyl)-acetamide (Compound D2)

LC-ESI-HRMS of [M+H]$^+$ shows 387,1631 Da. Calc. 387,163257 Da.

2-(3,5-Bis-trifluoromethyl-phenyl)-N-(4-oxo-2-thiazolidin-3-yl-4H-quinazolin-3-yl)-acetamide (Compound D3)

LC-ESI-HRMS of [M+H]$^+$ shows 503,0962 Da. Calc. 503,09764 Da.

2-Benzo[1,3]dioxol-5-yl-N-(2-diethylamino-4-oxo-4H-quinazolin-3-yl)-acetamide (Compound D4)

LC-ESI-HRMS of [M+H]$^+$ shows 395,1716 Da. Calc. 395,171931 Da.

Using Method E the following compound was synthesized

N-[2-(Ethyl-methyl-amino)-4-oxo-4H-quinazolin-3-yl]-2-phenyl-acetamide (Compound E2)

LC-ESI-HRMS of [M+H]$^+$ shows 337,167 Da. Calc. 337,166451 Da.

Using Method A0+B+C the following compounds were synthesized

N-[6-(tert-Butyl-dimethyl-silanyloxy)-2-diethylamino-4-oxo-4H-quinazolin-3-yl]-2-(3,5-difluoro-phenyl)-acetamide (Intermediate Compound)

{2-Diethylamino-3-[2-(3,5-difluoro-phenyl)-acetylamino]-4-oxo-3,4-dihydro-quinazolin-6-yl}-carbamic acid tert-butyl ester (Intermediate Compound)

(3-Amino-2-diethylamino-4-oxo-3,4-dihydro-quinazolin-7-yl)-carbamic acid tert-butyl ester (Intermediate Compound)

(3-Amino-4-oxo-2-pyrrolidin-1-yl-3,4-dihydro-quinazolin-7-yl)-carbamic acid tert-butyl ester (Intermediate Compound)

In addition the following compounds were synthesized

N-(2-Diethylamino-6-hydroxy-4-oxo-4H-quinazolin-3-yl)-2-(3,5-difluoro-phenyl)-acetamide (Compound F1)

N-[6-(tert-Butyl-dimethyl-silanyloxy)-2-diethylamino-4-oxo-4H-quinazolin-3-yl]-2-(3,5-difluoro-phenyl)-acetamide (1.50 g, 2.85 mmol) was dissolved in dry THF (50 mL). Tetrabutylammonium fluoride (1 M in THF, 3.13 mL, 3.13 mmol) was added to the mixture over 10 minutes at RT. Stirring was continued for 30 minutes. The solvent was removed in vacuo and the residue was subjected to column chromatography (EtOAc/Heptane) giving the title compound (0.60 g, 54%).

LC-ESI-HRMS of [M+H]$^+$ shows 403.158 Da. Calc. 403.158172 Da.

N-(6,8-Dichloro-2-diethylamino-4-oxo-4H-quinazolin-3-yl)-2-(3,5-difluoro-phenyl)-acetamide (Compound F2)

N-(2-Diethylamino-4-oxo-4H-quinazolin-3-yl)-2-(3,5-difluoro-phenyl)-acetamide (0.500 g, 1.26 mmol) was dissolved in acetonitrile (20 mL). The mixture was heated at 60° C. overnight. The solvent was removed in vacuo followed by addition of water. The aqueous layer was extracted with DCM and the combined organics were dried (MgSO$_4$) and evaporated. The residue was subjected to column chromatography (EtOAc/Heptane) giving the title compound (0.200 g, 35%).

LC-ESI-HRMS of [M+H]$^+$ shows 455.0864 Da. Calc. 455.085313 Da.

N-(6-Amino-2-diethylamino-4-oxo-4H-quinazolin-3-yl)-2-(3,5-difluoro-phenyl)-acetamide (Compound F3)

{2-Diethylamino-3-[2-(3,5-difluoro-phenyl)-acetylamino]-4-oxo-3,4-dihydro-quinazolin-6-yl}-carbamic acid tert-butyl ester was dissolved in 1 M HCl in acetic acid. The mixture was stirred at RT for 1 h. The mixture was evaporated to near dryness, followed by addition of diethyl ether. The formed precipitate was collected by filtration, washed with diethyl ether and dried to give the title compound as a hydrochloride salt (0.40 g, 77%).

LC-ESI-HRMS of [M+H]⁺ shows 402.1741 Da. Calc. 402.174156 Da.

Using the method from compound F3 the following compounds were synthesized

N-(7-Amino-2-diethylamino-4-oxo-4H-quinazolin-3-yl)-2-(3,5-difluoro-phenyl)-acetamide (Compound F4)

LC-ESI-HRMS of [M+H]⁺ shows 402.1743 Da. Calc. 402.174156 Da.

N-(7-Amino-4-oxo-2-pyrrolidin-1-yl-4H-quinazolin-3-yl)-2-(3,5-difluoro-phenyl)-acetamide (Compound F5)

LC-ESI-HRMS of [M+H]⁺ shows 400.1565 Da. Calc. 400.158506 Da.

Example 2

Biological Activity

In a standard patch-clamp set-up, e.g. as outlined in International Patent Publication WO 2004/080377, using HEK293 cell lines stably expressing the human $K_v7.2+K_v7.3$ channels, the compounds of the invention were found to be activators of the channels at various concentrations at various degrees.

The effect obtained by these channel activators is described as a percentage increase in baseline current at a given concentration. The baseline current is defined as 100%, and an increase in current is expressed relative to this, i.e. an increase from 1 nA to 1.2 nA is reported as 120%.

| Test compound | $I_K$ (%) at −30 mV, 1 s |
|---|---|
| C1 | 150 |
| C3 | 144 |
| C5 | 143 |
| C11 | 153 |
| C19 | 215 |
| D2 | 290 |
| F1 | 110 |

From the foregoing it will be appreciated that, although specific embodiments of the invention have been described herein for purposes of illustration, various modifications may be made without deviating from the spirit and scope of the invention. Accordingly, the invention is not to be limited as by the appended claims.

The features disclosed in the foregoing description, in the claims and/or in the accompanying drawings, may both separately and in any combination thereof, be material for realizing the invention in diverse forms thereof.

Preferred features of the invention:
1. A 2,3-diamino-quinazolinone derivative of Formula (I)

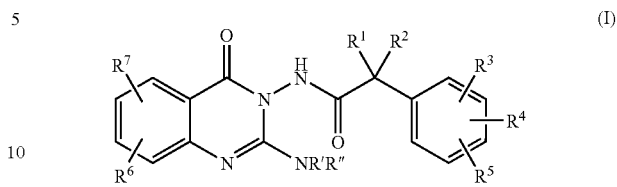

a stereoisomer or a mixture of its stereoisomers, or a pharmaceutically-acceptable addition salt thereof, or an N-oxide thereof, wherein
$R^1$ represents hydrogen, alkyl or halo; and
$R^2$ represents hydrogen, alkyl, cycloalkyl, halo, haloalkyl, hydroxyalkyl, hydroxy, alkoxy, phenyl, phenyl-alkyl, amino, alkyl-carbonyl-amino, cyano or nitro; or
$R^1$ and $R^2$ together with the carbon atom to which they are attached form a cycloalkyl (spiro) group; or
$R^1$ represents hydrogen; and $R^2$ together with one of $R^3$, $R^4$ and $R^5$, attached in ortho-position on the aromatic ring, form a —(CH$_2$)$_n$— bridge, wherein n is 1, 2 or 3;
$R^3$, $R^4$ and $R^5$, independently of each other, represent hydrogen, alkyl, cycloalkyl, halo, haloalkyl, hydroxy, alkoxy, haloalkoxy, amino, alkyl-carbonyl-amino, alkyl-sulfonyl, phenyl, benzoyl, cyano or nitro; or
two of $R^3$, $R^4$ and $R^5$, together form a methylenedioxy group; and the remaining of $R^3$, $R^4$ and $R^5$ is as defined above; or
one of $R^3$, $R^4$ and $R^5$, attached in ortho-position on the aromatic ring, and together with $R^2$ form a —(CH$_2$)$_n$— bridge, wherein n is 1, 2 or 3; and the remaining of $R^3$, $R^4$ and $R^5$, are as defined above;
$R^6$ and $R^7$, independently of each other, represent hydrogen, alkyl, cycloalkyl, halo, haloalkyl, hydroxy, alkoxy, haloalkoxy, amino, alkyl-carbonyl-amino, nitro, cyano or phenyl; and
R' and R", independently of each other, represent alkyl, hydroxy-alkyl, amino-alkyl, phenyl-alkyl, phenyl-hydroxyalkyl, N-alkyl-amino-alkyl, N,N-dialkyl-amino-alkyl, alkoxy-alkyl, phenyl-alkyl, piperidinyl, N-alkyl-piperidinyl, furanyl-alkyl, pyridinyl-alkyl, pyrazolyl-alkyl, imidazolyl-alkyl, pyrimidinyl, pyrimidinyl substituted with one or two substituents selected from N-alkyl-amino, N,N-dialkyl-amino and phenyl; or
R' and R", together with the nitrogen to which they are attached, form a heterocyclic ring selected from pyrrolidinyl, 2,5-dihydro-1H-pyrrol-1-yl, thiazolidinyl, piperidinyl, piperazinyl, homopiperazinyl and morpholinyl, which pyrrolidinyl, piperidinyl, piperazinyl, homopiperazinyl and morpholinyl is optionally substituted one or more times with a substituent selected from the group consisting of alkyl, alkoxy, alkoxy-alkyl, alkyl-carbonyl-amino, cycloalkyl-carbonyl-amino, hydroxy-alkyl, hydroxy, amino, N-alkyl-amino, N,N-dialkyl-amino, amino-alkyl, N-alkyl-amino-alkyl, N,N-dialkyl-amino-alkyl, carbamoyl-alkyl, N-alkyl-carbamoyl-alkyl, N,N-dialkyl-carbamoyl-alkyl, N-hydroxy-alkyl-carbamoyl, N,N-dialkyl-amino-alkyl-carbamoyl, alkoxy-carbonyl, cyano-alkyl, pyrrolidinyl, pyrrolidinyl-alkyl, piperidinyl, piperidinyl-alkyl, piperidinyl-carbonyl, hydroxy-piperidinyl, hydroxy-piperidinyl-alkyl, hydroxy-piperidinyl-carbonyl, piperazinyl, piperidinyl, N-alkyl-piperidinyl, piperidinyl-alkyl, N-alkyl-piperidinyl-alkyl, morpholino-alkyl, morpholino-alkyl-carbamoyl, morpholino-carbonyl-alkyl, triazolyl-alkyl, piperazinyl, piperazinyl-alkyl, piperazinyl-carbonyl, N-alkyl-piperazinyl, N-alkyl-piperazinyl-alkyl, N-alkyl-piperazinyl-carbonyl, pyridinyl, pyridinyl-alkyl, and pyridinyl substituted once or twice with alkyl, trifluoromethyl and/or cyano.

2. The 2,3-diamino-quinazolinone derivative of clause 1, or a pharmaceutically-acceptable addition salt thereof, or an N-oxide thereof, wherein $R^1$ represents hydrogen, alkyl or halo; and $R^2$ represents hydrogen, alkyl, cycloalkyl, halo, haloalkyl, hydroxyalkyl, hydroxy, alkoxy, phenyl, phenyl-alkyl, amino, alkyl-carbonyl-amino, cyano or nitro.

3. The 2,3-diamino-quinazolinone derivative of clause 1, or a pharmaceutically-acceptable addition salt thereof, or an N-oxide thereof, wherein $R^1$ and $R^2$ together with the carbon atom to which they are attached form a cycloalkyl (spiro) group.

4. The 2,3-diamino-quinazolinone derivative of clause 1, or a pharmaceutically-acceptable addition salt thereof, or an N-oxide thereof, wherein $R^1$ represents hydrogen; and $R^2$ together with one of $R^3$, $R^4$ and $R^5$, attached in ortho-position on the aromatic ring, form a —$(CH_2)_n$— bridge, wherein n is 1, 2 or 3.

5. The 2,3-diamino-quinazolinone derivative of any one of clauses 1-4, or a pharmaceutically-acceptable addition salt thereof, or an N-oxide thereof, wherein $R^3$, $R^4$ and $R^5$, independently of each other, represent hydrogen, alkyl, cycloalkyl, halo, haloalkyl, hydroxy, alkoxy, haloalkoxy, amino, alkyl-carbonyl-amino, alkyl-sulfonyl, phenyl, benzoyl, cyano or nitro.

6. The 2,3-diamino-quinazolinone derivative of any one of clauses 1-4, or a pharmaceutically-acceptable addition salt thereof, or an N-oxide thereof, wherein two of $R^3$, $R^4$ and $R^5$, together form a methylenedioxy group; and the remaining of $R^3$, $R^4$ and $R^5$ is as defined above.

7. The 2,3-diamino-quinazolinone derivative of any one of clauses 1-4, or a pharmaceutically-acceptable addition salt thereof, or an N-oxide thereof, wherein one of $R^3$, $R^4$ and $R^5$, attached in ortho-position on the aromatic ring, and together with $R^2$ form a —$(CH_2)_n$— bridge, wherein n is 1, 2 or 3; and the remaining of $R^3$, $R^4$ and $R^5$, are as defined above.

8. The 2,3-diamino-quinazolinone derivative of any one of clauses 1-7, or a pharmaceutically-acceptable addition salt thereof, or an N-oxide thereof, wherein $R^6$ and $R^7$, independently of each other, represent hydrogen, alkyl, cycloalkyl, halo, haloalkyl, hydroxy, alkoxy, haloalkoxy, amino, alkyl-carbonyl-amino (acetamido), nitro, cyano or phenyl.

9. The 2,3-diamino-quinazolinone derivative of any one of clauses 1-8, or a pharmaceutically-acceptable addition salt thereof, or an N-oxide thereof, wherein R' and R", independently of each other, represent alkyl, hydroxy-alkyl, amino-alkyl, phenyl-alkyl, phenyl-hydroxyalkyl, N-alkyl-amino-alkyl, N,N-dialkyl-amino-alkyl, alkoxy-alkyl, phenyl-alkyl, piperidinyl, N-alkyl-piperidinyl, furanyl-alkyl, pyridinyl-alkyl, pyrazolyl-alkyl, imidazolyl-alkyl, pyrimidinyl, pyrimidinyl substituted with one or two substituents selected from N-alkyl-amino, N,N-dialkyl-amino and phenyl.

10. The 2,3-diamino-quinazolinone derivative of clause 9, a stereoisomer or a mixture of its stereoisomers, or a pharmaceutically-acceptable addition salt thereof, or an N-oxide thereof, wherein R' represents alkyl; and R" represents alkyl, amino-alkyl, hydroxy-alkyl, N,N-dialkyl-amino-alkyl, N-alkyl-pyrrolidinyl, pyridinyl-alkyl or N-alkyl-piperidinyl.

11. The 2,3-diamino-quinazolinone derivative of any one of clauses 1-8, or a pharmaceutically-acceptable addition salt thereof, or an N-oxide thereof, wherein R' and R", together with the nitrogen to which they are attached, form a heterocyclic ring selected from pyrrolidinyl, 2,5-dihydro-1H-pyrrol-1-yl, thiazolidinyl, piperidinyl, piperazinyl, homopiperazinyl and morpholinyl, which pyrrolidinyl, piperidinyl, piperazinyl, homopiperazinyl and morpholinyl is optionally substituted one or more times with a substituent selected from the group consisting of alkyl, alkoxy, alkoxy-alkyl, alkyl-carbonyl-amino, cycloalkyl-carbonyl-amino, hydroxy-alkyl, hydroxy, amino, N-alkyl-amino, N,N-dialkyl-amino, amino-alkyl, N-alkyl-amino-alkyl, N,N-dialkyl-amino-alkyl, carbamoyl-alkyl, N-alkyl-carbamoyl-alkyl, N,N-dialkyl-carbamoyl-alkyl, N-hydroxy-alkyl-carbamoyl, N,N-dialkyl-amino-alkyl-carbamoyl, alkoxy-carbonyl, cyano-alkyl, pyrrolidinyl, pyrrolidinyl-alkyl, piperidinyl, piperidinyl-alkyl, piperidinyl-carbonyl, hydroxy-piperidinyl, hydroxy-piperidinyl-alkyl, hydroxy-piperidinyl-carbonyl, piperazinyl, piperidinyl, N-alkyl-piperidinyl, piperidinyl-alkyl, N-alkyl-piperidinyl-alkyl, morpholino-alkyl, morpholino-alkyl-carbamoyl, morpholino-carbonyl-alkyl, triazolyl-alkyl, piperazinyl, piperazinyl-alkyl, piperazinyl-carbonyl, N-alkyl-piperazinyl, N-alkyl-piperazinyl-alkyl, N-alkyl-piperazinyl-carbonyl, pyridinyl, pyridinyl-alkyl, and pyridinyl substituted once or twice with alkyl, trifluoromethyl and/or cyano.

12. The 2,3-diamino-quinazolinone derivative of clause 1, which is:
2-(3,5-Difluoro-phenyl)-N-(4-oxo-2-pyrrolidin-1-yl-4H-quinazolin-3-yl)-acetamide;
2-(3,5-Difluoro-phenyl)-N-(2-dimethylamino-4-oxo-4H-quinazolin-3-yl)-acetamide;
2-(4-Chloro-phenyl)-N-(2-diethylamino-4-oxo-4H-quinazolin-3-yl)-acetamide;
2-(3,5-Difluoro-phenyl)-N-[2-(ethyl-methyl-amino)-4-oxo-4H-quinazolin-3-yl]-acetamide;
2-(3,5-Difluoro-phenyl)-N-(2-dimethylamino-4-oxo-7-trifluoromethyl-4H-quinazolin-3-yl)-propionamide;
N-(2-Diethylamino-4-oxo-4H-quinazolin-3-yl)-2-(4-methanesulfonyl-phenyl)-acetamide;
N-{2-[(2-Methoxy-ethyl)-methyl-amino]-4-oxo-4H-quinazolin-3-yl}-2-(4-trifluoromethyl-phenyl)-acetamide;
2-(4-Butoxy-phenyl)-N-{2-[(2-methoxy-ethyl)-methyl-amino]-4-oxo-4H-quinazolin-3-yl}-acetamide;
N-[2-(Benzyl-methyl-amino)-4-oxo-4H-quinazolin-3-yl]-2-(4-methanesulfonyl-phenyl)-acetamide;
2-(4-Butoxy-phenyl)-N-(4-oxo-2-pyrrolidin-1-yl-4H-quinazolin-3-yl)-acetamide;
2-(3,5-Difluoro-phenyl)-N-(4-oxo-2-thiazolidin-3-yl-4H-quinazolin-3-yl)-acetamide;
N-(2-Diethylamino-4-oxo-4H-quinazolin-3-yl)-2-(3,5-difluoro-phenyl)-acetamide;
2-(3,5-Bis-trifluoromethyl-phenyl)-N-(4-oxo-2-thiazolidin-3-yl-4H-quinazolin-3-yl)-acetamide;
2-Benzo[1,3]dioxol-5-yl-N-(2-diethylamino-4-oxo-4H-quinazolin-3-yl)-acetamide;
N-(2-Diethylamino-4-oxo-4H-quinazolin-3-yl)-2-phenyl-acetamide; or
N-[2-(Ethyl-methyl-amino)-4-oxo-4H-quinazolin-3-yl]-2-phenyl-acetamide; or
a pharmaceutically-acceptable addition salt thereof.

13. A pharmaceutical composition comprising a therapeutically effective amount of the 2,3-diamino-quinazolinone derivative of any one of clauses 1-12, or a pharmaceutically-acceptable addition salt thereof 14. Use of the 2,3-diamino-quinazolinone derivative of any one of clauses 1-12, or a pharmaceutically-acceptable addition salt thereof, for the manufacture of a pharmaceutical composition/medicament.

15. Use of the 2,3-diamino-quinazolinone derivative of any one of clauses 1-12, or a pharmaceutically-acceptable addition salt thereof, for the manufacture of a pharmaceutical composition for the treatment, prevention or alleviation of a disease or a disorder or a condition of a mammal, including a human, which disease, disorder or condition is responsive to activation of $K_v7$ channels.

16. The use according to clause 15, wherein the disease, disorder or condition is pain, neurodegenerative disorders, migraine, bipolar disorders, mania, epilepsy, convulsions, seizures and seizure disorders, anxiety, depression, functional bowel disorders and multiple sclerosis.

17. The use according to clause 15, wherein the disease, disorder or condition is pain, mild, moderate or severe pain, acute, chronic or recurrent pain, neuropathic pain, pain caused by migraine, postoperative pain, phantom limb pain, neuropathic pain, chronic headache, tension type headache, central pain, pain related to diabetic neuropathy, to post therapeutic neuralgia, or to peripheral nerve injury.

18. The use according to clause 15, wherein the disease, disorder or condition is pain, neuropathic pain, epilepsy or anxiety.

19. A method of treatment, prevention or alleviation of a disease or a disorder or a condition of a living animal body, including a human, which disorder, disease or condition is responsive to activation of $K_v7$ channels, which method comprises the step of administering to such a living animal body in need thereof, a therapeutically effective amount of the 2,3-diamino-quinazolinone derivative of any one of claims 1-12, or a pharmaceutically-acceptable addition salt thereof.

The invention claimed is:
1. A 2,3-diamino-quinazolinone compound of Formula (I)

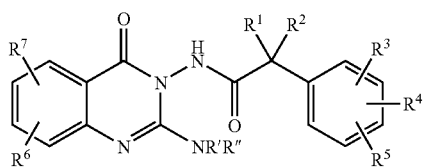

(I)

a stereoisomer or a mixture of its stereoisomers, or a pharmaceutically-acceptable addition salt thereof, or an N-oxide thereof, wherein $R^1$ represents hydrogen, alkyl or halo; and $R^2$ represents hydrogen, alkyl, cycloalkyl, halo, haloalkyl, hydroxy-alkyl, hydroxy, alkoxy, phenyl, phenyl-alkyl, amino, alkyl-carbonyl-amino, cyano or nitro; or $R^1$ and $R^2$ together with the carbon atom to which they are attached form a cycloalkyl (spiro) group; or $R^1$ represents hydrogen; and $R^2$ together with one of $R^3$, $R^4$ and $R^5$, attached in ortho-position on the aromatic ring, form a —$(CH_2)_n$— bridge, wherein n is 1, 2 or 3;

$R^3$, $R^4$ and $R^5$, independently of each other, represent hydrogen, alkyl, cycloalkyl, halo, haloalkyl, hydroxy, alkoxy, haloalkoxy, amino, alkyl-carbonyl-amino, alkyl-sulfanyl, alkyl-sulfonyl, phenyl, phenoxy, benzoyl, cyano or nitro; or two of $R^3$, $R^4$ and $R^5$, together form a methylenedioxy group; and the remaining of $R^3$, $R^4$ and $R^5$ is as defined above; or two of $R^3$, $R^4$ and $R^5$, together with the phenyl ring to which they are attached, form a naphthyl group; and the remaining of $R^3$, $R^4$ and $R^5$ is as defined above; or one of $R^3$, $R^4$ and $R^5$, attached in ortho-position on the aromatic ring, and together with $R^2$ form a —$(CH_2)_n$— bridge, wherein n is 1, 2 or 3; and the remaining of $R^3$, $R^4$ and $R^5$, are as defined above;

$R^6$ and $R^7$, independently of each other, represent hydrogen, alkyl, cycloalkyl, halo, haloalkyl, hydroxy, alkoxy, haloalkoxy, amino, alkyl-carbonyl-amino, nitro, cyano or phenyl; and R' and R", independently of each other, represent alkyl, hydroxy-alkyl, amino-alkyl, cycloalkyl, phenyl-alkyl, phenyl-hydroxyalkyl, N-alkyl-amino-alkyl, N,N-dialkyl-amino-alkyl, alkoxy-alkyl, piperidinyl, N-alkyl-piperidinyl, furanyl-alkyl, pyridinyl-alkyl, pyrazolyl-alkyl, imidazolyl-alkyl, pyrimidinyl, pyrimidinyl substituted with one or two substituents selected from N-alkyl-amino, N,N-dialkyl-amino and phenyl; or R' and R", together with the nitrogen to which they are attached, form a heterocyclic ring selected from pyrrolidinyl, 2,5-dihydro-1H-pyrrol-1-yl, thiazolidinyl, piperidinyl, piperazinyl, homopiperazinyl, morpholinyl and homomorpholinyl, which pyrrolidinyl, piperidinyl, piperazinyl, homopiperazinyl, morpholinyl and homomorpholinyl is optionally substituted one or more times with a substituent selected from the group consisting of alkyl, alkoxy, alkoxy-alkyl, alkyl-carbonyl-amino, cycloalkyl-carbonyl-amino, hydroxy-alkyl, hydroxy, amino, N-alkyl-amino, N,N-dialkyl-amino, amino-alkyl, N-alkyl-amino-alkyl, N,N-dialkyl-amino-alkyl, carbamoyl-alkyl, N-alkyl-carbamoyl-alkyl, N,N-dialkyl-carbamoyl-alkyl, N-hydroxy-alkyl-carbamoyl, N,N-dialkyl-amino-alkyl-carbamoyl, alkoxy-carbonyl, cyano-alkyl, pyrrolidinyl, pyrrolidinyl-alkyl, piperidinyl, piperidinyl-carbonyl, hydroxy-piperidinyl, hydroxy-piperidinyl-alkyl, hydroxy-piperidinyl-carbonyl, N-alkyl-piperidinyl, piperidinyl-alkyl, N-alkyl-piperidinyl-alkyl, morpholino-alkyl, morpholino-alkyl-carbamoyl, morpholino-carbonyl-alkyl, triazolyl-alkyl, piperazinyl, piperazinyl-alkyl, piperazinyl-carbonyl, N-alkyl-piperazinyl, N-alkyl-piperazinyl-alkyl, N-alkyl-piperazinyl-carbonyl, pyridinyl, pyridinyl-alkyl, and pyridinyl substituted once or twice with alkyl, trifluoromethyl and/or cyano.

2. The 2,3-diamino-quinazolinone compound of claim 1, a stereoisomer or a mixture of its stereoisomers, or a pharmaceutically-acceptable addition salt thereof, or an N-oxide thereof, wherein $R^1$ represents hydrogen or alkyl; and $R^2$ represents hydrogen or alkyl.

3. The 2,3-diamino-quinazolinone compound of claim 1, a stereoisomer or a mixture of its stereoisomers, or a pharmaceutically-acceptable addition salt thereof, or an N-oxide thereof, wherein $R^3$, $R^4$ and $R^5$, independently of each other, represent hydrogen, alkyl, halo, haloalkyl, hydroxy, alkoxy, alkyl-sulfanyl, alkyl-sulfonyl, phenyl or phenoxy.

4. The 2,3-diamino-quinazolinone compound of claim 1, a stereoisomer or a mixture of its stereoisomers, or a pharmaceutically-acceptable addition salt thereof, or an N-oxide thereof, wherein $R^6$ and $R^7$, independently of each other, represent hydrogen, halo, haloalkyl, hydroxy, alkoxy, or amino.

5. The 2,3-diamino-quinazolinone compound of claim 1, a stereoisomer or a mixture of its stereoisomers, or a pharmaceutically-acceptable addition salt thereof, or an N-oxide thereof, wherein R' and R", independently of each other, represent alkyl, hydroxy-alkyl, cycloalkyl, or phenyl-alkyl.

6. The 2,3-diamino-quinazolinone compound of claim 1, a stereoisomer or a mixture of its stereoisomers, or a pharmaceutically-acceptable addition salt thereof, or an N-oxide thereof, wherein R' and R", together with the nitrogen to which they are attached, form a heterocyclic ring selected from pyrrolidinyl, thiazolidinyl, piperidinyl, piperazinyl, homopiperazinyl and morpholinyl, which piperazinyl is optionally substituted one or more times with alkyl.

7. The 2,3-diamino-quinazolinone compound of claim 1, which is:
- 2-(3,5-Difluoro-phenyl)-N-(4-oxo-2-pyrrolidin-1-yl-4H-quinazolin-3-yl)-acetamide;
- 2-(3,5-Difluoro-phenyl)-N-(2-dimethylamino-4-oxo-4H-quinazolin-3-yl)-acetamide;
- 2-(4-Chloro-phenyl)-N-(2-diethylamino-4-oxo-4H-quinazolin-3-yl)-acetamide;
- 2-(3,5-Difluoro-phenyl)-N-[2-(ethyl-methyl-amino)-4-oxo-4H-quinazolin-3-yl]-acetamide;
- 2-(3,5-Difluoro-phenyl)-N-(2-dimethylamino-4-oxo-7-trifluoromethyl-4H-quinazolin-3-yl)-propionamide;
- N-(2-Diethylamino-4-oxo-4H-quinazolin-3-yl)-2-(4-methanesulfonyl-phenyl)-acetamide;
- N-{2-[(2-Methoxy-ethyl)-methyl-amino]-4-oxo-4H-quinazolin-3-yl}-2-(4-trifluoromethyl-phenyl)-acetamide;
- 2-(4-Butoxy-phenyl)-N-{2-[(2-methoxy-ethyl)-methyl-amino]-4-oxo-4H-quinazolin-3-yl}-acetamide;
- N-[2-(Benzyl-methyl-amino)-4-oxo-4H-quinazolin-3-yl]-2-(4-methanesulfonyl-phenyl)-acetamide;
- 2-(4-Butoxy-phenyl)-N-(4-oxo-2-pyrrolidin-1-yl-4H-quinazolin-3-yl)-acetamide;
- 2-(3,5-Difluoro-phenyl)-N-(4-oxo-2-thiazolidin-3-yl-4H-quinazolin-3-yl)-acetamide;
- N-(2-Diethylamino-4-oxo-4H-quinazolin-3-yl)-2-(3,5-difluoro-phenyl)-acetamide;
- 2-(3,5-Bis-trifluoromethyl-phenyl)-N-(4-oxo-2-thiazolidin-3-yl-4H-quinazolin-3-yl)-acetamide;
- 2-Benzo[1,3]dioxol-5-yl-N-(2-diethylamino-4-oxo-4H-quinazolin-3-yl)-acetamide;
- N-(2-Diethylamino-4-oxo-4H-quinazolin-3-yl)-2-phenyl-acetamide; or
- N-[2-(Ethyl-methyl-amino)-4-oxo-4H-quinazolin-3-yl]-2-phenyl-acetamide; or a stereoisomer or a mixture of its stereoisomers, a pharmaceutically-acceptable addition salt thereof.

8. The 2,3-diamino-quinazolinone compound of claim 1, which is:
- 2-(3-Fluoro-4-trifluoromethyl-phenyl)-N-(4-oxo-2-pyrrolidin-1-yl-4H-quinazolin-3-yl)-acetamide;
- 2-(3,5-Bis-trifluoromethyl-phenyl)-N-{2-[(2-methoxy-ethyl)-methyl-amino]-4-oxo-4H-quinazolin-3-yl}-acetamide;
- N-[2-(Benzyl-methyl-amino)-4-oxo-4H-quinazolin-3-yl]-2-(3,4-difluoro-phenyl)-acetamide;
- 2-(3,5-Difluoro-phenyl)-N-(2-morpholin-4-yl-4-oxo-4H-quinazolin-3-yl)-acetamide;
- 2-(4-Chloro-phenyl)-N-{7-fluoro-2-[(2-methoxy-ethyl)-methyl-amino]-4-oxo-4H-quinazolin-3-yl}-acetamide;
- 2-(4-Chloro-phenyl)-N-(2-morpholin-4-yl-4-oxo-4H-quinazolin-3-yl)-acetamide;
- 2-(3,5-Difluoro-phenyl)-N-{7-fluoro-2-[(2-methoxy-ethyl)-methyl-amino]-4-oxo-4H-quinazolin-3-yl}-acetamide;
- 2-(4-Chloro-phenyl)-N-(2-dimethylamino-4-oxo-4H-quinazolin-3-yl)-acetamide;
- N-(2-Diethylamino-6-fluoro-4-oxo-4H-quinazolin-3-yl)-2-(3,5-difluoro-phenyl)-acetamide;
- 2-(4-Chloro-phenyl)-N-(2-diethylamino-6-fluoro-4-oxo-4H-quinazolin-3-yl)-acetamide;
- 2-(3,5-Difluoro-phenyl)-N-[2-(4-methyl-piperazin-1-yl)-4oxo-4H-quinazolin-3-yl]-acetamide;
- N-(2-Diethylamino-6-fluoro-4-oxo-4H-quinazolin-3-yl)-2-(3-fluoro-5-trifluoromethyl-phenyl)-acetamide;
- N-[2-(Benzyl-methyl-amino)-4-oxo-4H-quinazolin-3-yl]-2-(3,5-difluoro-phenyl)-acetamide;
- 2-(3,5-Difluoro-phenyl)-N-{2-[(2-methoxy-ethyl)-methyl-amino]-4-oxo-4H-quinazolin-3-yl}-acetamide;
- 2-(3-Fluoro-5-trifluoromethyl-phenyl)-N-(4-oxo-2-pyrrolidin-1-yl-7-trifluoromethyl-4H-quinazolin-3-yl)-acetamide;
- 2-(3,5-Difluoro-phenyl)-N-(4-oxo-2-pyrrolidin-1-yl-7-trifluoromethyl-4H-quinazolin-3-yl)-acetamide;
- 2-(3-Fluoro-5-trifluoromethyl-phenyl)-N-{2-[(2-methoxy-ethyl)-methyl-amino]-4-oxo-7-trifluoromethyl-4H-quinazolin-3-yl}-acetamide;
- 2-(3,5-Difluoro-phenyl)-N-{2-[(2-methoxy-ethyl)-methyl-amino]-4-oxo-7-trifluoromethyl-4H-quinazolin-3-yl}-acetamide;
- N-(6-Butoxy-2-morpholin-4-yl-4-oxo-4H-quinazolin-3-yl)-2-(3,5-difluoro-phenyl)-acetamide;
- N-(5-Chloro-4-oxo-2-pyrrolidin-1-yl-4H-quinazolin-3-yl)-2-(3,5-difluoro-phenyl)-acetamide;
- N-(5-Chloro-2-diethylamino-4-oxo-4H-quinazolin-3-yl)-2-(3,5-difluoro-phenyl)-acetamide;
- N-(2-Diethylamino-7-fluoro-4-oxo-4H-quinazolin-3-yl)-2-(3,5-difluoro-phenyl)-acetamide;
- N-(2-Diethylamino-5-fluoro-4-oxo-4H-quinazolin-3-yl)-2-(3,5-difluoro-phenyl)-acetamide;
- N-(2-Diethylamino-4-oxo-7-trifluoromethyl-4H-quinazolin-3-yl)-2-(3,5-difluoro-phenyl)-acetamide;
- N-(7-Chloro-2-diethylamino-4-oxo-4H-quinazolin-3-yl)-2-(3,5-difluoro-phenyl)-acetamide;
- N-(7-Chloro-4-oxo-2-pyrrolidin-1-yl-4H-quinazolin-3-yl)-2-(3,5-difluoro-phenyl)-acetamide;
- N-(6-Chloro-2-diethylamino-7-fluoro-4-oxo-4H-quinazolin-3yl)-2-(3,5-difluoro-phenyl)-acetamide;
- N-(2-Diethylamino-5,7-difluoro-4-oxo-4H-quinazolin-3-yl)-2-(3,5-difluoro-phenyl)-acetamide;
- 2-(3,5-Difluoro-phenyl)-N-(7-fluoro-4-oxo-2-pyrrolidin-1-yl-4H-quinazolin-3-yl)-acetamide;
- N-(6-Chloro-7-fluoro-4-oxo-2-pyrrolidin-1-yl-4H-quinazolin-3-yl)-2-(3,5-difluoro-phenyl)-acetamide;
- N-(5,7-Difluoro-4-oxo-2-pyrrolidin-1-yl-4H-quinazolin-3-yl)-2-(3,5-difluoro-phenyl)-acetamide;
- N-(5,7-Dichloro-2-diethylamino-4-oxo-4H-quinazolin-3-yl)-2-(3,5-difluoro-phenyl)-acetamide;
- N-(2-Diethylamino-6,7-difluoro-4-oxo-4H-quinazolin-3-yl)-2-(3,5-difluoro-phenyl)-acetamide;
- N-(6,7-Difluoro-4-oxo-2-pyrrolidin-1-yl-4H-quinazolin-3-yl)-2-(3,5-difluoro-phenyl)-acetamide;
- 2-(3-Fluoro-4-trifluoromethyl-phenyl)-N-(2-morpholin-4-yl-4-oxo-4H-quinazolin-3-yl)-acetamide;
- N-(2-Dimethylamino-4-oxo-4H-quinazolin-3-yl)-2-(3-fluoro-4-trifluoromethyl-phenyl)-acetamide;
- N-(6-Chloro-2-diethylamino-4-oxo-4H-quinazolin-3-yl)-2-(3,5-difluoro-phenyl)-acetamide;
- N-(2-Dimethylamino-6-fluoro-4-oxo-4H-quinazolin-3-yl)-2-(3-fluoro-4-trifluoromethyl-phenyl)-acetamide;
- N-(6-Fluoro-4-oxo-2-pyrrolidin-1-yl-4H-quinazolin-3-yl)-2-(3-fluoro-4-trifluoromethyl-phenyl)-acetamide;
- 2-(4-Chloro-3-fluoro-phenyl)-N-(6-fluoro-4-oxo-2-pyrrolidin-1-yl-4H-quinazolin-3-yl)-acetamide;

2-(3,5-Difluoro-phenyl)-N-(6-fluoro-4-oxo-2-pyrrolidin-1-yl-4H-quinazolin-3-yl)-acetamide;
2-(4-Chloro-3-fluoro-phenyl)-N-(2-dimethylamino-6-fluoro-4-oxo-4H-quinazolin-3-yl)-acetamide;
2-(3,5-Difluoro-phenyl)-N-(2-dimethylamino-6-fluoro-4-oxo-4H-quinazolin-3-yl)-acetamide;
N-(5,7-Dichloro-4-oxo-2-pyrrolidin-1-yl-4H-quinazolin-3-yl)-2-(3,5-difluoro-phenyl)-acetamide;
2-(3,5-Difluoro-phenyl)-N-(2-dimethylamino-5-fluoro-4-oxo-4H-quinazolin-3-yl)-acetamide;
2-(3,5-Difluoro-phenyl)-N-(2-dimethylamino-7-fluoro-4-oxo-4H-quinazolin-3-yl)-acetamide;
N-(2-Dimethylamino-5-fluoro-4-oxo-4H-quinazolin-3-yl)-2-(3-fluoro-5-trifluoromethyl-phenyl)-acetamide;
N-(2-Dimethylamino-7-fluoro-4-oxo-4H-quinazolin-3-yl)-2-(3-fluoro-4-trifluoromethyl-phenyl)-acetamide;
2-(4-Chloro-phenyl)-N-(2-diethylamino-5,7-difluoro-4-oxo-4-quinazolin-3-yl)-acetamide;
2-(4-Chloro-phenyl)-N-(7-fluoro-4-oxo-2-pyrrolidin-1yl-4H-quinazolin-3-yl)-acetamide;
2-(3,5-Difluoro-phenyl)-N-[5-fluoro-2-(isopropyl-methyl-amino)-4-oxo-4H-quinazolin-3-yl]-acetamide;
2-(3,5-Difluoro-phenyl)-N-[2-(ethyl-methyl-amino)-5-fluoro-4-oxo-4H-quinazolin-3-yl]-acetamide;
2-(3,5-Difluoro-phenyl)-N-[7-fluoro-2-(isopropyl-methyl-amino)-4-oxo-4H-quinazolin-3-yl]-acetamide;
2-(3,5-Difluoro-phenyl)-N-[2-(ethyl-methyl-amino)-7-fluoro-4-oxo-4H-quinazolin-3-yl]-acetamide;
2-(4-Chloro-phenyl)-N-(7-fluoro-4-oxo-2-pyrrolidin-1-yl-4H-quinazolin-3-yl)-propionamide;
2-(4-Chloro-phenyl)-N-(4-oxo-2-pyrrolidin-1-yl-4H-quinazolin-3-yl)-propionamide;
N-(2-Diethylamino-8-fluoro-4-oxo-4H-quinazolin-3-yl)-2-(3,5-difluoro-phenyl)-acetamide;
2-(3,5-Difluoro-phenyl)-N-(8-fluoro-4-oxo-2-pyrrolidin-1-yl-4H-quinazolin-3-yl)-acetamide;
2-Naphthalen-2-yl-N-(4-oxo-2-pyrrolidin-1-yl-4H-quinazolin-3-yl)-acetamide;
N-(5,7-Difluoro-4-oxo-2-pyrrolidin-1-yl-4H-quinazolin-3-yl)-2-(3,4-difluoro-phenyl)-acetamide;
2-(3,4-Difluoro-phenyl)-N-[2-(ethyl-methyl-amino)-7-fluoro-4-oxo-4H-quinazolin-3-yl]-acetamide;
2-(4-Chloro-phenyl)-N-[2-(ethyl-methyl-amino)-7-fluoro-4-oxo-4H-quinazolin-3-yl]-acetamide;
2-Naphthalen-1-yl-N-(4-oxo-2-pyrrolidin-1-yl-4H-quinazolin-3-yl)-acetamide;
2-(4-Chloro-phenyl)-N-(5,7-difluoro-4-oxo-2-pyrrolidin-1-yl-4H-quinazolin-3-yl)-acetamide;
2-(3,5-Difluoro-phenyl)-N-[2-(ethyl-methyl-amino)-5,7-difluoro-4-oxo-4H-quinazolin-3-yl]-acetamide;
N-[5,7-Difluoro-2-(isopropyl-methyl-amino)-4-oxo-4H-quinazolin-3-yl]-2-(3,4-difluoro-phenyl)-acetamide;
N-[5,7-Difluoro-2-(isopropyl-methyl-amino)-4-oxo-4H-quinazolin-3-yl]-2-(3,5-difluoro-phenyl)-acetamide;
N-[2-(Ethyl-methyl-amino)-7-fluoro-4-oxo-4H-quinazolin-3-yl]-2-(4-methylsulfanyl-phenyl)-acetamide;
2-(4-Isobutyl-phenyl)-N-(4-oxo-2-pyrrolidin-1-yl-4H-quinazolin-3-yl)-propionamide;
N-[2-(Ethyl-methyl-amino)-7-fluoro-4-oxo-4H-quinazolin-3-yl]-2-(4-methoxy-phenyl)-acetamide;
N-(7-Fluoro-4-oxo-2-pyrrolidin-1-yl-4H-quinazolin-3-yl)-2-(4-phenoxy-phenyl)-acetamide;
2-Biphenyl-4-yl-N-(7-fluoro-4-oxo-2-pyrrolidin-1-yl-4H-quinazolin-3-yl)-acetamide;
2-(4-Chloro-phenyl)-N-(4-oxo-2-pyrrolidin-1-yl-4H-quinazolin-3-yl)-acetamide;
2-(3,4-Difluoro-phenyl)-N-(4-oxo-2-pyrrolidin-1-yl-4H-quinazolin-3-yl)-acetamide;
N-[2-(Ethyl-methyl-amino)-7-fluoro-4-oxo-4H-quinazolin-3-yl]-2-(4-isopropyl-phenyl)-acetamide;
2-(3,5-Difluoro-phenyl)-N-[2-(isopropyl-methyl-amino)-4-oxo-4-quinazolin-3-yl]-acetamide;
2-(3,4-Difluoro-phenyl)-N-[2-(isopropyl-methyl-amino)-4-oxo-4H-quinazolin-3-yl]-acetamide;
2-(3,4-Difluoro-phenyl)-N-(7-fluoro-4-oxo-2-pyrrolidin-1-yl-4H-quinazolin-3-yl)-acetamide;
2-(3,4-Difluoro-phenyl)-N-(8-fluoro-4-oxo-2-pyrrolidin-1-yl-4H-quinazolin-3-yl)-acetamide;
2-(3,4-Difluoro-phenyl)-N-[2-(isobutyl-methyl-amino)-4-oxo-4H-quinazolin-3-yl]-acetamide;
2-(3,5-Difluoro-phenyl)-N-[2-(isobutyl-methyl-amino)-4-oxo-4H-quinazolin-3-yl]-acetamide;
2-(3,4-Difluoro-phenyl)-N-[7-fluoro-2-(isopropyl-methyl-amino)-4-oxo-4H-quinazolin-3-yl]-acetamide;
N-(7-Chloro-6-fluoro-4-oxo-2-pyrrolidin-1-yl-4H-quinazolin-3-yl)-2-(3,5-difluoro-phenyl)-acetamide;
2-(3,5-Difluoro-phenyl)-N-(2-diisopropylamino-4-oxo-4H-quinazolin-3-yl)-acetamide;
N-[2-(Cyclopentyl-methyl-amino)-4-oxo-4H-quinazolin-3-yl]-2-(3,5-difluoro-phenyl)-acetamide;
N-[2-(Cyclopentyl-methyl-amino)-4-oxo-4H-quinazolin-3-yl]-2-(3,4-difluoro-phenyl)-acetamide;
2-(3,4-Difluoro-phenyl)-N-(2-diisopropylamino-4-oxo-4H-quinazolin-3-yl)-acetamide;
2-(3,4-Difluoro-phenyl)-N-(4-oxo-2-piperidin-1-yl-4H-quinazolin-3-yl)-acetamide;
2-(3,5-Difluoro-phenyl)-N-(4-oxo-2-piperidin-1-yl-4H-quinazolin-3-yl)-acetamide;
N-(8-Chloro-4-oxo-2-pyrrolidin-1-yl-4H-quinazolin-3-yl)-2-(3,5-difluoro-phenyl)-acetamide;
N-(2-Diethylamino-6-hydroxy-4-oxo-4H-quinazolin-3-yl)-2-(3,5-difluoro-phenyl)-acetamide;
N-(6,8-Dichloro-2-diethylamino-4-oxo-4H-quinazolin-3-yl)-2-(3,5-difluoro-phenyl)-acetamide;
N-(6-Amino-2-diethylamino-4-oxo-4H-quinazolin-3-yl)-2-(3,5-difluoro-phenyl)-acetamide;
N-(7-Amino-2-diethylamino-4-oxo-4H-quinazolin-3-yl)-2-(3,5-difluoro-phenyl)-acetamide;
N-(7-Amino-4-oxo-2-pyrrolidin-1-yl-4H-quinazolin-3-yl)-2-(3,5-difluoro-phenyl)-acetamide; or
a stereoisomer or a mixture of its stereoisomers, a pharmaceutically-acceptable addition salt thereof.

9. A pharmaceutical composition comprising a therapeutically effective amount of the 2,3-diamino-quinazolinone compound of claim 1, a stereoisomer or a mixture of its stereoisomers, or a pharmaceutically-acceptable addition salt thereof.

10. The 2,3-diamino-quinazolinone compound of claim 7, which is:
2-(3,5-difluorophenyl)-N-(2-dimethylamino-4-oxo-7-trifluoromethyl-4H-quinazolin-3-yl )-propionamide; or
a stereoisomer or a mixture of its stereoisomers, or a pharmaceutically-acceptable addition salt thereof.

* * * * *